US012663391B2

(12) United States Patent (10) Patent No.: US 12,663,391 B2
Gardner et al. (45) Date of Patent: Jun. 23, 2026

(54) THERMAL CONDUCTIVITY FLUID SENSOR

(71) Applicant: Flusso Limited, Cambridge (GB)

(72) Inventors: Ethan Gardner, Warwickshire (GB);
Sean Dixon, Cambridgeshire (GB);
Florin Udrea, Cambridgeshire (GB);
Syed Zeeshan Ali, Cambridgeshire
(GB)

(73) Assignee: FLUSSO LIMITED, Cambridgeshire
(GB)

( * ) Notice: Subject to any disclaimer, the term of this
patent is extended or adjusted under 35
U.S.C. 154(b) by 320 days.

(21) Appl. No.: 18/394,258

(22) Filed: Dec. 22, 2023

(65) Prior Publication Data

US 2025/0208077 A1 Jun. 26, 2025

(51) Int. Cl.
G01N 25/18 (2006.01)
G01N 33/00 (2006.01)

(52) U.S. Cl.
CPC ......... G01N 25/18 (2013.01); G01N 33/0031
(2013.01)

(58) Field of Classification Search
CPC .... G01N 25/18; G01N 25/20; G01N 33/0031;
G01N 33/0036; G01N 33/0059
See application file for complete search history.

(56) References Cited

U.S. PATENT DOCUMENTS 8,265,881 B1 * 9/2012 Lakhotia ............ G01N 33/0059
204/406
8,689,608 B2 4/2014 Nakano et al.

9,140,659 B2 9/2015 De Coulon et al.
10,429,330 B2 10/2019 Le Neel et al.
2020/0088669 A1 3/2020 König
2022/0136988 A1 5/2022 Kamiyama et al.

(Continued)

FOREIGN PATENT DOCUMENTS

EP 2290357 A1 3/2011
JP 2007155502 A 6/2007
JP 2016170161 A 9/2016

(Continued)

OTHER PUBLICATIONS

Computer translation of JP_2020_173144_A (Year: 2025).*

(Continued)

*Primary Examiner* — Randy W Gibson
(74) *Attorney, Agent, or Firm* — Fisher Broyles, LLP

(57) ABSTRACT

A thermal conductivity fluid sensor for detecting a first
component of a mixture, the thermal conductivity fluid
sensor comprising: a first heating element; and a controller,
the controller configured to: control a temperature of the first
heating element such that the temperature of the first heating
element changes from a first temperature to a second tem-
perature over a first transient time period; obtain a first
reading indicative of a first thermal transport property of the
mixture during the first transient time period; obtain a
second reading indicative of second thermal transport prop-
erty of the mixture when the first heating element is at the
second temperature; and determine, based on the first read-
ing and the second reading, a concentration of the first
component of the mixture. A method for determining a
concentration of a component of a mixture is also described.

20 Claims, 18 Drawing Sheets

(56)      References Cited

U.S. PATENT DOCUMENTS

2022/0404300 A1    12/2022   Ali et al.

FOREIGN PATENT DOCUMENTS

| | | | |
|---|---|---|---|
| JP | 2020173144 A | 10/2020 | |
| JP | 7155192 B2 | 10/2022 | |
| WO | WO-9852027 A1 * | 11/1998 | ............ G01N 25/56 |
| WO | 2018034948 A1 | 2/2018 | |

OTHER PUBLICATIONS

Computer translation of WO_9852027_A1 (Year: 2025).*
Search Report and Written Opinion from corresponding LU application No. 505904, dated Jul. 11, 2024, 8 pages.

* cited by examiner

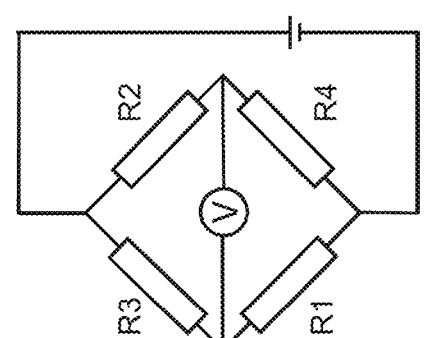
Figure 11A
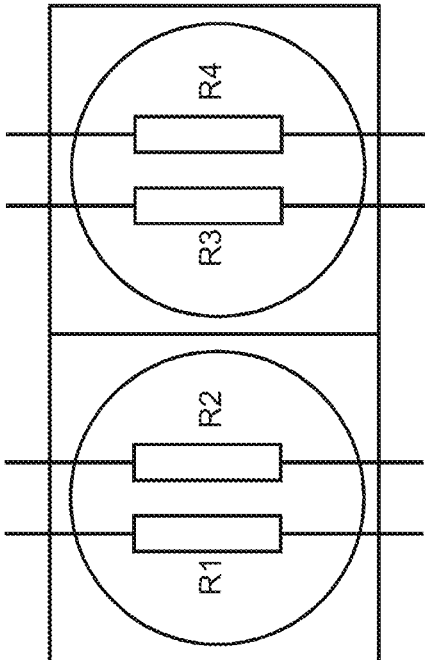
Figure 11B
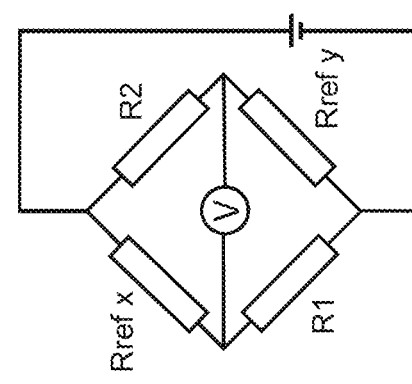
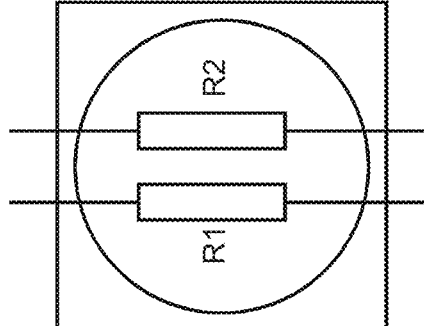

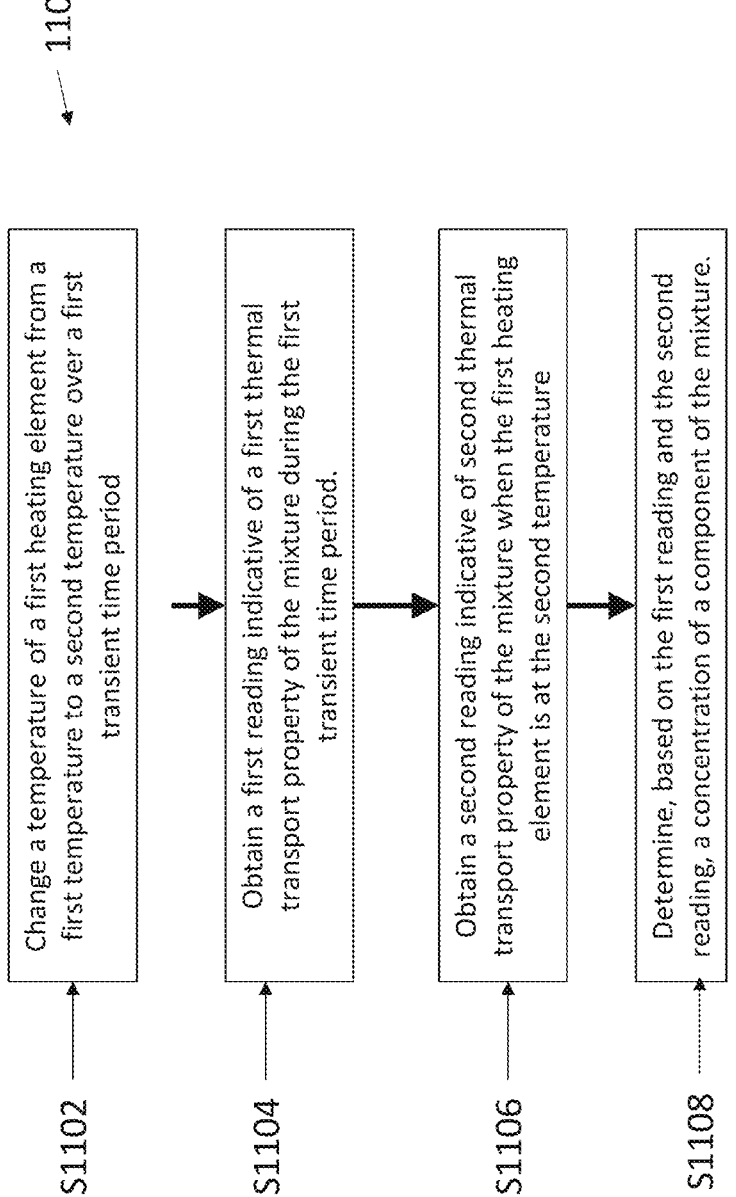

1100

S1102 — Change a temperature of a first heating element from a first temperature to a second temperature over a first transient time period S1104 — Obtain a first reading indicative of a first thermal transport property of the mixture during the first transient time period.

S1106 — Obtain a second reading indicative of second thermal transport property of the mixture when the first heating element is at the second temperature S1108 — Determine, based on the first reading and the second reading, a concentration of a component of the mixture.

Figure 13

THERMAL CONDUCTIVITY FLUID SENSOR

TECHNICAL FIELD

The present disclosure relates to thermal conductivity fluid sensors. In particular, the present disclosure relates to detecting a first component of a gas mixture (e.g. humidity).

BACKGROUND

Thermal conductivity fluid sensors may be used to identify a target gas and its concentration.

Applications of thermal conductivity fluid sensors include air quality monitoring, gas leak detection, explosive/toxic gas detection (measure LEL; lower explosive level); hydrogen cell/station monitoring, lithium ion battery failure detection, food storage atmospheric control, natural gas monitoring. Thermal conductivity fluid sensors also provide a nonflammable method of measuring, which is advantageous for measuring explosive gases such as hydrogen ($H_2$), methane ($CH_4$), etc.

Humidity is a strong parasitic for thermal conductivity fluid sensors; target gas readings may be strongly affected unless humidity in the environment is measured and/or compensated for. Most known methods for measuring humidity measure relative humidity, RH (e.g. % RH), and tend not to be very accurate.

At present, a parasitic component such as humidity may be detected by using mainly three different types of device:

1. Capacitive humidity sensors measure relative humidity by placing a thin strip of metal oxide or polymer between two electrodes. Sensing surface is coated with a porous metal electrode and substrate is typically glass, ceramic or silicon. Its operation depends on the dielectric property of water molecules that are sandwiched between the two layers of conductive metal, therefore changing capacitance between the two electrodes.

2. Resistive humidity sensors measure relative humidity by measuring the electrical impedance of a hygroscopic medium such as a conductive polymer, salt or treated substrate.

3. Thermal humidity sensors measure the absolute humidity by quantifying the difference between thermal conductivity of dry air and that of air containing water vapor.

In each of the above cases, an extra sensor is needed in the sensing system, e.g. a carbon dioxide ($CO_2$) sensing system, including a thermal conductivity fluid sensor to detect $CO_2$ (or another target gas), to compensate for varying humidity if the sensor is to be used in exposed ambient environments.

The readings of those separate devices are used to correct the reading of the sensor used to detect the target gas. In some other cases, a humidity sensor may be added as a separate feature of the thermal conductivity fluid sensor using a different technology from the technology used in the thermal conductivity fluid sensor. Having a separate device or a separate feature using a separate technology in order to detect a second component or a parasitic component of a gas mixture, adds complexity to the sensing solution and increases costs. Furthermore, using different devices may negatively affect the accuracy of the measurements.

SUMMARY

In some applications, it may be advantageous to detect more than one component of a mixture of gas components with the same thermal conductivity fluid sensor, in order to have more compact sensing solutions and at reduced costs. In some applications, such as but not limited to natural gas monitoring, the two components may be two target components such as methane and carbon dioxide.

In other applications, such as, but not limited to, detection of a gas in the presence of humidity, a first component may be a target component while a second component may be a parasitic component which affects the detection of the target component so decreasing the accuracy of the response of the thermal conductivity fluid sensor.

As an example, $CO_2$ may be a target component while humidity (i.e. water vapor) may be a parasitic component for a thermal conductivity fluid sensor for the detection of $CO_2$ in air.

It will be understood that atmospheric air may be present in the mixture of gas components and that, in some instances, a first and/or a second component may be a gas which is part of the atmospheric air, for example humidity and/or $CO_2$. The first component and/or the second component may be a gas present in atmospheric air but in a different concentration. In other instances the first component and/or the second component may not be gases present in atmospheric air.

Using the thermal conductivity principle allows the measurement of absolute humidity, which provides greater resolution at high humidities compared with relative humidity measurement. If the sensor that measures the gas also measures the humidity, it may measure a highly localized humidity and thus can compensate the sensor as accurately as possible.

The present disclosure provides a thermal conductivity fluid sensor for detecting a first component of a gas mixture, the thermal conductivity fluid sensor comprising:

a first heating element; and a controller, the controller configured to:

control a temperature of the first heating element such that the temperature of the first heating element changes from a first temperature to a second temperature over a first transient time period;

obtain a first reading indicative of a first thermal transport property of the gas mixture during the first transient time period;

obtain a second reading indicative of second thermal transport property of the gas mixture when the first heating element is at the second temperature; and determine, based on the first reading and the second reading, a concentration of the first component of the gas mixture.

It will be understood that as used herein, controlling a temperature of a heating element so that it is set at a pre-determined value (e.g. a first temperature, a second temperature or any other temperature) may mean applying a fixed bias to the heating element such that, if the heating element were in a calibration environment, the heating element would reach the pre-determined temperature. When the heating element is in a different environment, the heating element may not reach the pre-determined temperature, when applied the corresponding bias. The actual temperature reached by the heating element is indicative of the nature and/or composition of the environment to which it is exposed.

It will be further understood that as used herein, controlling a temperature of a heating element so that it is set at a pre-determined value (e.g. a first temperature, a second temperature or any other temperature) may mean applying a variable bias to the heating element such that the heating element will reach the pre-determined temperature irrespective of the environment to which it is exposed. In this case, the actual bias will be different from the bias applied to the heating element to reach the pre-determined temperature in the calibration environment, depending on the nature and composition of the environment to which the heating element is exposed. The actual bias applied so that the heating element reaches the pre-determined temperature is indicative of the nature and/or composition of the environment to which it is exposed.

A pre-determined temperature, may mean a specific temperature value (e.g. 100° C., 300° C., 500° C. or any other suitable temperature value) independent of external conditions (e.g. independent of the ambient temperature), or it may mean a relative temperature, for example defined based on a pre-determined difference with respect to the ambient temperature (for example 100° C., 300° C., 500° C. or any other suitable amount above ambient temperature) or with respect to another temperature, as appropriate.

For example, the controller may be configured to determine a contribution of a first component of the gas mixture to a temperature dependent thermal response of the gas mixture based on the first reading and the second reading. The controller may be configured to determine the concentration of the first component of the gas mixture based on the contribution of the first component of the gas mixture to the temperature dependent thermal response of the gas mixture.

It will be understood that a contribution of a first (or a second) component of the gas mixture to a temperature dependent thermal response of the gas mixture, means a portion of the thermal response of the gas mixture. It will further be understood that said contribution or portion is a function of the concentration of the first (or second) component.

The second reading may be obtained when the first heating element is in a steady state at the second temperature (e.g. while the temperature of the first heating element is not changing, or has finished changing, e.g. at the end of the first transient time period).

Once the contribution of the first component is determined, it may be used to calculate the contribution of a second component of the gas mixture to a temperature dependent thermal response of the gas mixture and, in turn, the concentration of the second component of the mixture. For this purpose, a new reading may be obtained preferably in conditions where the contribution of the second component of the gas mixture to a temperature dependent thermal response of the gas mixture is higher than the contribution of the first component, e.g. where the difference between the two contributions is the largest in the fluid sensor operational temperature range.

It will be understood that the thermal conductivity fluid sensor of the disclosure will be calibrated for the first component and for the second component of the mixture.

Advantageously, a thermal conductivity fluid sensor according to the present disclosure enables the measurement of an absolute concentration of the component of the gas mixture (where the component may comprise humidity).

Further advantageously, where the first component comprises humidity, this can be detected using the thermal conductivity fluid sensor described herein without the need for a separate humidity sensor. That is, humidity can be detected using the same fluid sensor as the fluid sensor using for the target gas detection/sensing.

The thermal conductivity fluid sensor according to the present disclosure also enables localized measurement of the humidity. In cases where a separate humidity sensor is employed, the humidity measurement would be performed at a different location to the gas measurement. In the case of the present disclosure, the gas measurement and the humidity measurement can be performed in one location at a same humidity, enabling improved spatial and temporal measurement of parasitics.

Furthermore, the thermal conductivity fluid sensor described herein may exhibit improved accuracy at high temperatures and/or humidities. For example, relative humidity measurements can lose accuracy at high water vapor concentrations, and the absolute humidity sensor enabled by the present disclosure would not suffer from this.

In addition, the thermal conductivity fluid sensor described herein may exhibit a larger operating range, and may exhibit reduced poisoning of chemical/binding material surfaces.

A "reading" as described herein may correspond to a sensed temperature of the gas mixture. A reading may be obtained from the heating element (e.g. the heating element may be configured to operate as a temperature sensor), and/or a reading may be obtained from a temperature sensing element. A reading may correspond to a recorded temperature of a heating element. E.g., a reading may be a reading of the temperature of a heating element, or a reading may be a reading of a voltage across a heating element, and/or a reading of a current and/or power supplied to the heating element and/or a reading of a resistance of the heating element.

The controller may be configured to record the temperature of the first heating element while the temperature of the first heating element changes from the first temperature to the second temperature over the first transient time period. For example, the controller may record the temperature of the first heating element at a plurality of times during the first transient time period, so as to obtain a larger amount of data which may result in a more accurate sensor response. In some examples, the controller may take an integral of the change in temperature of the first heating element over time during the first transient time period.

The first thermal transport property of the gas mixture may be a thermal diffusivity of the gas mixture.

The second thermal transport property of the gas mixture may be a thermal conductivity of the gas mixture.

Thermal transport properties of gases (or fluids, in general) change from one gas to another. Besides, for a specific gas, the thermal transport behaviour changes between a transient state and a steady state, and with temperature.

The present inventors are now proposing to use those differences to identify a first component, and its concentration, from a gas mixture and use such finding to identify a second component, from the gas mixture, and its concentration, so decoupling a contribution of a first component of the gas mixture and a contribution of a second component of the gas mixture to a temperature dependent thermal response of the gas mixture.

In some examples, the second temperature is higher than the first temperature.

In some examples, the second temperature is lower than the first temperature.

In some examples, the first temperature may be ambient temperature, i.e. the temperature of the heating element when the heating element is not powered, or, in other words, when the applied voltage is zero, and changing the temperature from a first temperature to a second temperature may mean switching the heating element on and heating it to a second temperature, higher than ambient temperature.

In other examples, the second temperature may be ambient temperature and the first temperature may be higher than ambient temperature. In those cases, changing the temperature from a first temperature to a second temperature may mean switching the heating element off or simply lower the applied voltage (or current or power) so as to cool the heating element to a second temperature substantially equal to ambient temperature.

The controller may be configured to obtain the first reading at a predetermined time during the first transient time period.

The predetermined time may preferably be a time at which the contribution of the first component to the temperature dependent thermal response of the gas mixture is higher than the contribution of the second component to the temperature dependent thermal response of the gas mixture. More preferably, the predetermined time may be a time at which the difference in said contribution is the largest during the first transient time.

The second temperature may preferably be a temperature at which the contribution of the first component to the temperature dependent thermal response of the gas mixture is higher than the contribution of the second component to the temperature dependent thermal response of the gas mixture. More preferably, the second temperature may be a temperature at which the difference in said contribution is the largest in the sensor operational temperature range.

The controller may be further configured to:

control the temperature of the first heating element such that the temperature of the first heating element changes from the second temperature to a third temperature over a second transient time period;

obtain a third reading indicative of a third thermal transport property of the gas mixture during the second transient time period, or when the heating element is at the third temperature; and determine, based additionally on the third reading, the concentration of the component of the gas mixture.

For example, the controller may be configured to determine the contribution of a first component of the gas mixture to a temperature dependent thermal response of the gas mixture based additionally on the third reading. As described above, the controller may be configured to determine the concentration of the first component of the gas mixture based on the contribution of the component of the gas mixture to the temperature dependent thermal response of the gas mixture.

The third reading may be obtained when the first heating element is in a steady state at the third temperature.

Since the thermal transport properties of a gas also change with temperature, obtaining further readings at different temperatures may allow to obtain more accurate sensor responses, and in turn, more accurate concentration values for the first and, consequently, the second component of the gas mixture.

The third temperature may be higher than the second temperature. The third temperature may be lower than the second temperature.

The third thermal transport property of the gas mixture may be the thermal diffusivity of the gas mixture or thermal conductivity of the gas mixture.

In some instances, the third temperature may be the same as the first temperature.

In some examples, the third temperature may be the same as the first temperature and the third reading may be obtained during the second transient time period. The thermal transport behaviour of a gas in a thermal transient state may be different depending on the sense of the change of the temperature. The thermal transport behaviour during a heating transient time period may be different from the thermal transport behaviour during a cooling transient time period, i.e. while the temperature of the heating element changes from a first temperature from a second temperature and vice-versa; for example, a cooling transient time period may be shorter than a heating transient time period.

It will be understood that the first transient period length may be pre-determined for example, at least in part, by setting a pre-determined heating or cooling rate) a or it may not be pre-determined, for example when the voltage (or power or current) applied to the first heating element is set to zero.

The first reading, the second reading, and/or the third reading may be obtained for the gas mixture using the first heating element.

In some examples, the thermal conductivity fluid sensor may comprise a second heating element. The second heating element may be thermally insulated from the first heating element.

In some examples, the second heating element may be located in a sealed chamber (e.g. such that the second heating element is isolated from the gas mixture). The sealed chamber may contain a reference environment (or reference atmosphere, for example, the second heating element may be referred to as a reference heating element). The reference environment may be a vacuum, or may be a controlled atmosphere. For clarity, the environment to which the first heating element is exposed, including the gas mixture, may be defined a measured environment or measured atmosphere.

The controller may be configured, for each reading obtained using the first heating element, to obtain a corresponding reading using the second heating element. For example, corresponding readings may be taken, or obtained, at the same time and/or at the same temperature using the first and the second heating elements.

For example, the controller may be configured to: control a temperature of the second heating element such that the temperature of the second heating element changes from the first temperature to the second temperature over the first transient time period; obtain a first reference reading indicative of a first thermal transport property of the reference environment during the first transient time period; obtain a second reference reading indicative of a second thermal transport property of the reference environment when the second heating element is at the second temperature; and determine the concentration of the component of the gas mixture based additionally on the first reference reading and the second reference reading.

Using the second heating element as a reference heating element in this way may enable, for example, compensation for variations in environmental temperature.

The thermal conductivity fluid sensor may comprise a cap layer, the cap layer having a first cap portion disposed over the first heating element, and a second cap portion disposed over the second heating element. The second cap portion forms part of the sealed chamber. The first cap portion may be provided with an opening such that the first heating element is in fluid communication with an external environment, comprising the gas mixture.

The controller may also be configured to: control a temperature of the second heating element such that the temperature of the second heating element changes from the second temperature to the third temperature over the second transient time period; obtain a third reference reading indicative of a third thermal transport property of the reference environment during the second transient time period or when the second heating element is at the third temperature; and determine the concentration of the component of the gas mixture based additionally on the third reference reading.

In some examples, the second heating element (which may be thermally insulated from the first heating element) may be in fluid communication with the gas mixture and may be employed to obtain one or more additional readings of the gas mixture.

The controller may be configured to: control a temperature of the second heating element such that the temperature of the second heating element changes from a fourth temperature to a fifth temperature over a further first transient time period, the fifth temperature being different from the second temperature; and obtain a fourth reading indicative of a fourth thermal transport property of the gas mixture during the first transient time period or when the second heating element is at the fourth temperature.

The first and the further first transient time periods may be the same length, i.e. the first heating element may reach the second temperature at substantially the same time as the second heating element reaches the fifth temperature, or they may be of a different length, as appropriate.

This may allow to collect a higher number of readings in the unit of time, as they may be collected in parallel, or substantially in parallel with the first transient time period overlapping, at least in part, with the further first transient time period, making the response of the sensor more accurate and faster with respect to examples where the controller is configured to collect further readings in sequence, one after the other.

For example, the fourth reading may be obtained for the gas mixture using the second heating element.

The fourth reading (and any other additional readings) obtained using the second heating element may independently provide information on the concentration of the component of the gas mixture. In some examples, the fourth reading may be used in combination with any of the first, second, and third readings to obtain a differential measurement.

The fourth reading may be obtained when the second heating element is in a steady state at the fifth temperature.

The fourth temperature may be equal to the second temperature. The fifth temperature may be equal to the first temperature.

The first heating element may have a first structural composition, and the second heating element may have a second structural composition different from the first structural composition. The first and second structural compositions may comprise different materials and/or different dimensions, for example meaning that the first heating element and the second heating element are optimised for different temperature ranges.

For example, the first heating element and the second heating element may be composed from different materials. For example, the first heating element and the second heating element may have different physical dimensions.

The first heating element may comprise two heater portions. The second heater element may comprise two heater portions. For each of the first and/or second heating elements, the two heater portions may be integrated into a Wheatstone bridge read-out circuit. This may increase the sensitivity of the sensor as the module of the differential response is doubled.

Also described herein a method for determining a concentration of a first component of a gas mixture, the method comprising:

changing a temperature of a first heating element from a first temperature to a second temperature over a first transient time period;

obtaining a first reading indicative of a first thermal transport property of the gas mixture during the first transient time period;

obtaining a second reading indicative of a second thermal transport property of the gas mixture when the first heating element is at the second temperature; and determining, based on the first reading and the second reading, a concentration of the first component of the gas mixture.

For example, the method may comprise determining a contribution of a first component of the gas mixture to a temperature dependent thermal response of the gas mixture based on the first reading and the second reading. The method may comprise determining the concentration of the first component of the gas mixture based on the contribution of the first component of the gas mixture to the temperature dependent thermal response of the gas mixture.

The method may be carried out using a thermal conductivity fluid sensor as described herein.

The second reading may be obtained when the first heating element is in a steady state at the second temperature (e.g. while the temperature of the first heating element is not changing, or has finished changing, e.g. at the end of the first transient time period).

Once the contribution of the first component is determined, the method may further comprise using it to calculate the contribution of a second component of the gas mixture to a temperature dependent thermal response of the gas mixture and, in turn, the concentration of the second component of the mixture. For this purpose, a new reading may be obtained preferably in conditions where the contribution of the second component of the gas mixture to a temperature dependent thermal response of the gas mixture is higher than the contribution of the first component, e.g. where the difference between the two contributions is the largest in the sensor operational temperature range.

It will be understood that determining the concentration of the first component and, in turn of the second component of the gas mixture may comprise referring to calibration values or curves obtained for the first component and the second component.

Advantageously, the method according to the present disclosure enables the measurement of an absolute concentration of the component of the gas mixture (where the component may comprise humidity).

Further advantageously, where the first component comprises humidity, this can be detected using the method described herein using a single thermal conductivity fluid sensor. That is, humidity can be detected using a same fluid sensor as the fluid sensor used for target gas detection/sensing.

The method according to the present disclosure also enables localized measurement of the humidity. In cases where a separate humidity sensor is employed, the humidity measurement would be performed at a different location to the gas measurement. In the case of the present disclosure, the gas measurement and the humidity measurement can be performed in one location at a same humidity, enabling improved spatial and temporal measurement of parasitics.

Furthermore, the method described herein may exhibit improved accuracy at high temperatures and/or humidities.

For example, relative humidity measurements can lose accuracy at high water vapor concentrations, and the absolute humidity sensor enabled by the present disclosure would not suffer from this.

A "reading" as described herein may correspond to a sensed temperature of the gas mixture. A reading may be obtained from the heating element (e.g. the heating element may be configured to operate as a temperature sensor), and/or a reading may be obtained from a temperature sensing element. A reading may correspond to a recorded temperature of a heating element. E.g., a reading may be a reading of the temperature of a heating element, or a reading may be a reading of a voltage across a heating element, and/or a reading of a current and/or power supplied to the heating element, and/or a reading of a resistance of the heating element.

The method may comprise recording the temperature of the first heating element while the temperature of the first heating element changes from the first temperature to the second temperature over the first transient time period. For example, the method may comprise recording the temperature of the first heating element at a plurality of times during the first transient time period, so as to obtain a larger amount of data which may result in a more accurate sensor response. In some examples, the controller may take an integral of the change in temperature of the first heating element over time during the first transient time period.

The first thermal transport property of the gas mixture may be a thermal diffusivity of the gas mixture.

The second thermal transport property of the gas mixture may be a thermal conductivity of the gas mixture.

Thermal transport properties of gases (or fluids, in general) change from one gas to another. Besides, for a specific gas, the thermal transport behaviour changes between a transient state and a steady state, and with temperature.

The present inventors are now proposing to use those differences to identify a first component, and its concentration, from a mixture and use such finding to identify a second component, from the gas mixture, and its concentration, so decoupling a contribution of a first component of the gas mixture and a contribution of a second component of the gas mixture to a temperature dependent thermal response of the gas mixture.

In some examples, the second temperature is higher than the first temperature.

In some examples, the second temperature is lower than the first temperature.

In some examples, the first temperature may be ambient temperature, i.e. the temperature of the heating element when the heating element is not powered, or, in other words, when the applied voltage is zero, and changing the temperature from a first temperature to a second temperature may mean switching the heating element on and heating it to a second temperature, higher than ambient temperature.

In other examples, the second temperature may be ambient temperature and the first temperature may be higher than ambient temperature. In those cases, changing the temperature from a first temperature to a second temperature may mean switching the heating element off or simply lower the applied voltage (or current or power) so as to cool the heating element to a second temperature substantially equal to ambient temperature.

The method may comprise obtaining the first reading at a predetermined time during the first transient time period.

The predetermined time may preferably be a time at which the contribution of the first component to the temperature dependent thermal response of the gas mixture is higher than the contribution of the second component to the temperature dependent thermal response of the gas mixture. More preferably, the predetermined time may be a time at which the difference in said contribution is the largest in during the first transient time.

The second temperature may preferably be a temperature at which the contribution of the first component to the temperature dependent thermal response of the gas mixture is higher than the contribution of the second component to the temperature dependent thermal response of the gas mixture. More preferably, the second temperature may be a temperature at which the difference in said contribution is the largest in the sensor operational temperature range.

The method may further comprise:
changing the temperature of the first heating element from the second temperature to a third temperature over a second transient time period;
obtaining a third reading indicative of a third thermal transport property of the gas mixture during the second transient time period, or when the heating element is at the third temperature; and
determining, based additionally on the third reading, the concentration of the component of the gas mixture.

For example, the method may comprise determining the contribution of a first component of the gas mixture to a temperature dependent thermal response of the gas mixture based additionally on the third reading. As described above, the method may comprise determining the concentration of the first component of the gas mixture based on the contribution of the component of the gas mixture to the temperature dependent thermal response of the gas mixture.

The third reading may be obtained when the first heating element is in a steady state at the third temperature.

Since the thermal transport properties of a gas also change with temperature, obtaining further readings at different temperatures may allow to obtain more accurate sensor responses, and in turn, more accurate concentration values for the first and, consequently, the second component of the gas mixture.

The third temperature may be higher than the second temperature. The third temperature may be lower than the second temperature.

The third thermal transport property of the gas mixture may be the thermal diffusivity of the gas mixture or thermal conductivity of the gas mixture.

In some instances, the third temperature may be the same as the first temperature.

In some examples the third temperature may be the same as the first temperature and the third reading may be obtained during the second transient time period. The thermal transport behaviour of a gas in a thermal transient state may be different depending on the sense of the change of the temperature. The thermal transport behaviour during a heating transient time period may be different from the thermal transport behaviour during a cooling transient time period, i.e. while the temperature of the heating element changes from a first temperature from a second temperature and vice-versa; for example a cooling transient time period may be shorter than a heating transient time period.

It will be understood that the first transient period length may be pre-determined for example, at least in part, by setting a pre-determined heating or cooling rate, or it may not be pre-determined, for example when the voltage (or power or current) applied to the first heating element is set to zero by switching the heating element off.

The first reading, the second reading, and/or the third reading may be obtained for the gas mixture using the first heating element.

In some examples, the method may comprise changing a temperature of a second heating element from the first temperature to the second temperature over the first transient time period, the second heating element being thermally insulated from the first heating element and located in a reference environment; obtaining a first reference reading indicative of a first thermal transport property of the reference environment during the first transient time period; obtaining a second reference reading indicative of a second thermal transport property of the reference environment when the second heating element is at the second temperature; and determining the concentration of the component of the gas mixture based additionally on the first reference reading and the second reference reading In some examples, the second heating element may be located in a sealed chamber (e.g. such that the second heating element is isolated from the gas mixture). The sealed chamber may contain the reference environment (or reference atmosphere, for example, the second heating element may be referred to as a reference heating element). The reference environment may be a vacuum, or may be a controlled atmosphere. For clarity, the environment to which the first heating element is exposed, including the gas mixture, may be defined a measured environment or measured atmosphere.

The method may comprise obtaining, for each reading obtained using the first heating element, a corresponding reading using the second heating element. For example, corresponding readings may be taken, or obtained, at the same time and/or at the same temperature using the first and the second heating element.

Using the second heating element as a reference heating element in this way may enable, for example, compensation for variations in environmental temperature.

The controller may also be configured to: control a temperature of the second heating element such that the temperature of the second heating element changes from the second temperature to the third temperature over the second transient time period; obtain a third reference reading indicative of a third thermal transport property of the reference environment during the second transient time period or when the second heating element is at the third temperature; and determine the concentration of the component of the gas mixture based additionally on the third reference reading.

In some examples, the second heating element (which may be thermally insulated from the first heating element) may be in fluid communication with the gas mixture and may be employed to obtain one or more additional readings of the gas mixture.

In those cases, the method may further comprise: changing a temperature of a second heating element from a fourth temperature to a fifth temperature over a further first transient time period, the fifth temperature being different from the second temperature, the second heating element being thermally insulated from the first heating element; and obtaining a fourth reading indicative of a fourth thermal transport property of the gas mixture during the first transient time period or when the second heating element is at the fourth temperature.

The first and the further first transient time periods may be the same length, i.e. the first heating element may reach the second temperature at substantially the same time as the second heating element reaches the fifth temperature, or they may be of a different length, as appropriate.

This may allow to collect a higher number of readings in the unit of time, as they may be collected in parallel, or substantially in parallel with the first transient time period overlapping, at least in part, with the further first transient time period, making the response of the sensor more accurate and faster with respect to examples where further readings are collected in sequence, one after the other.

For example, the fourth reading may be obtained for the gas mixture using the second heating element.

The fourth reading (and any other additional readings) obtained using the second heating element may independently provide information on the concentration of the component of the gas mixture. In some examples, the fourth reading may be used in combination with any of the first, second, and third readings to obtain a differential measurement.

The fourth reading may be obtained when the second heating element is in a steady state at the fifth temperature.

The fourth temperature may be equal to the second temperature. The fifth temperature may be equal to the first temperature.

BRIEF DESCRIPTION OF THE DRAWINGS

The present invention will now be described by way of example with reference to the following drawings:

FIGS. 11A and 11B illustrate examples of how heating elements comprising two semi-elements, may be connected in a Wheatstone bridge;

FIG. 13 illustrates an example of a method for determining a concentration of a component of a mixture according to the present disclosure.

DETAILED DESCRIPTION

Figure 1A:
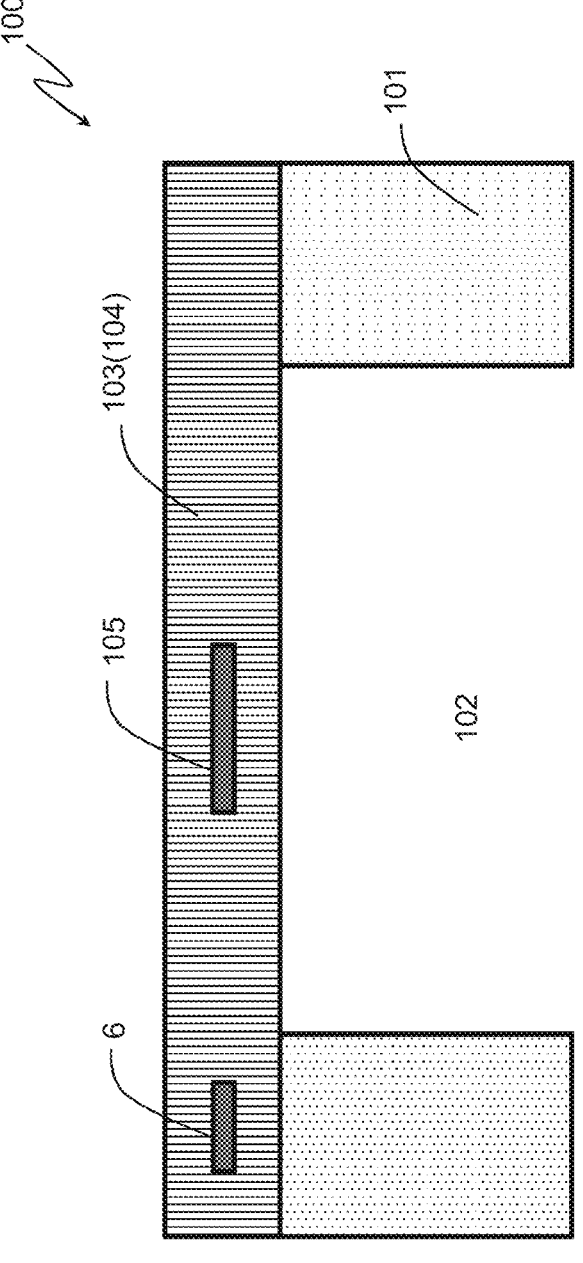
FIG. 1A schematically illustrates a cross-section of an example of a thermal conductivity fluid sensor according to the present disclosure.
Figure 1B:
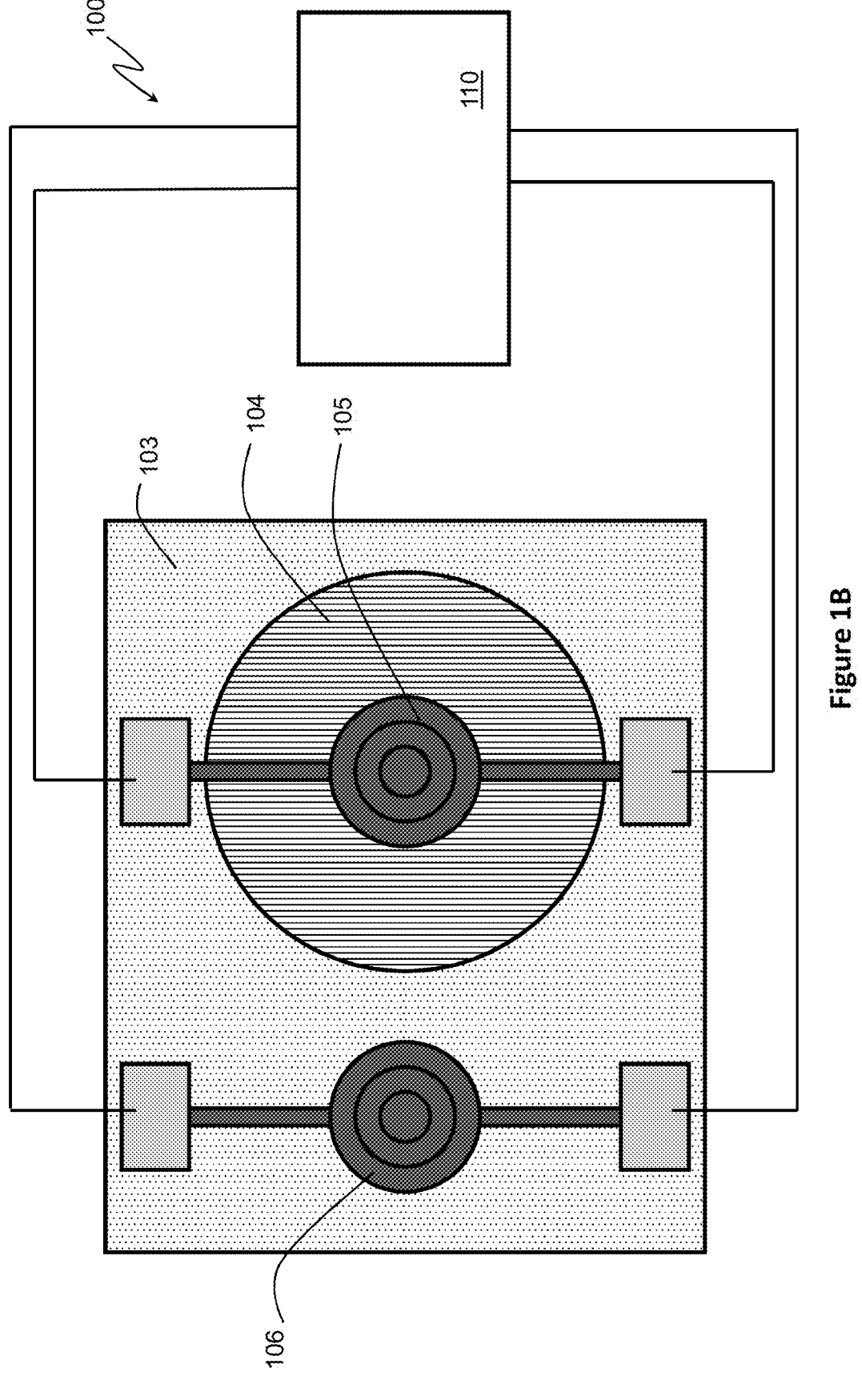
FIG. 1B schematically illustrates a top view of the example thermal conductivity fluid sensor illustrated in FIG. 1A.

FIG. 1A provides a cross-section of an example of a thermal conductivity fluid sensor 100 according to an embodiment of the disclosure. FIG. 1B is a top view of the thermal conductivity fluid sensor of FIG. 1A.

The thermal conductivity fluid sensor 100 comprises a substrate 101, for example comprising a semiconductor, such as silicon (Si), a cavity 102 and dielectric layer 103. The dielectric layer may comprise one or more layers and may comprise silicon dioxide, silicon nitride and/or any other suitable material or combination of materials. The dielectric layer 103 comprises a dielectric membrane 104 extending above the cavity 102. The thermal conductivity fluid sensor 100 further comprises a heating element 105. The heating element 105 may be a resistor and it may comprise platinum (Pt), tungsten (W), polysilicon or the like and any other suitable material, especially materials which are compatible with CMOS technology.

The heating element 105 may also function as the temperature sensing element. In other examples, the temperature sensing element may be distinct form the heating element and provided to the membrane at a determined distance from the heating element. The temperature sensing element, or temperature sensor may be a resistor, a thermopile, a thermos-couple or a diode. The temperature sensing element may comprise any suitable material, especially a material compatible with CMOS technology.

The thermal conductivity fluid sensor 100 additionally comprises a further temperature sensing element 106 provided outside of the membrane 104, which may be an environmental (or ambient) temperature sensing element. The temperature sensing element 106 may be located far enough from the heating element 105 so that it cannot sense the temperature of the heating element 105 and it may be used to compensate the sensor's readings for variations in the environmental temperature or to independently measure the ambient temperature. The further temperature sensing element 106 may not be provided in some examples of the thermal conductivity fluid sensor.

It will be understood that, even though the heating element 105 and the further temperature sensing element 106 are shown as microplates, this is not limiting and other kinds of heating elements and/or temperature sensing elements may be used instead, such as a wire, a serpentine and any other suitable component known in the art.

The thermal conductivity fluid sensor 100 also comprises a controller 110 which may be configured to determine the concentration of two components of a gas mixture based on their thermal conductivity, so that the controller may:

(a) Set the temperature of the heating element 105 in turn at two or more temperature bias;

(b) Take a reading at each temperature value, wherein at least one of the temperature bias is different from a nominal temperature bias;

(c) Determine the signal produced by the second component based on the combination of at least two of the readings taken at (b);

(d) Set the temperature of the heating element 105 at the nominal temperature bias;

(e) Take a reading at the nominal temperature;

(f) Correct the reading at the nominal temperature for the signal of the second component obtained at (e), so as to obtain a signal for the first component.

Figure 2:
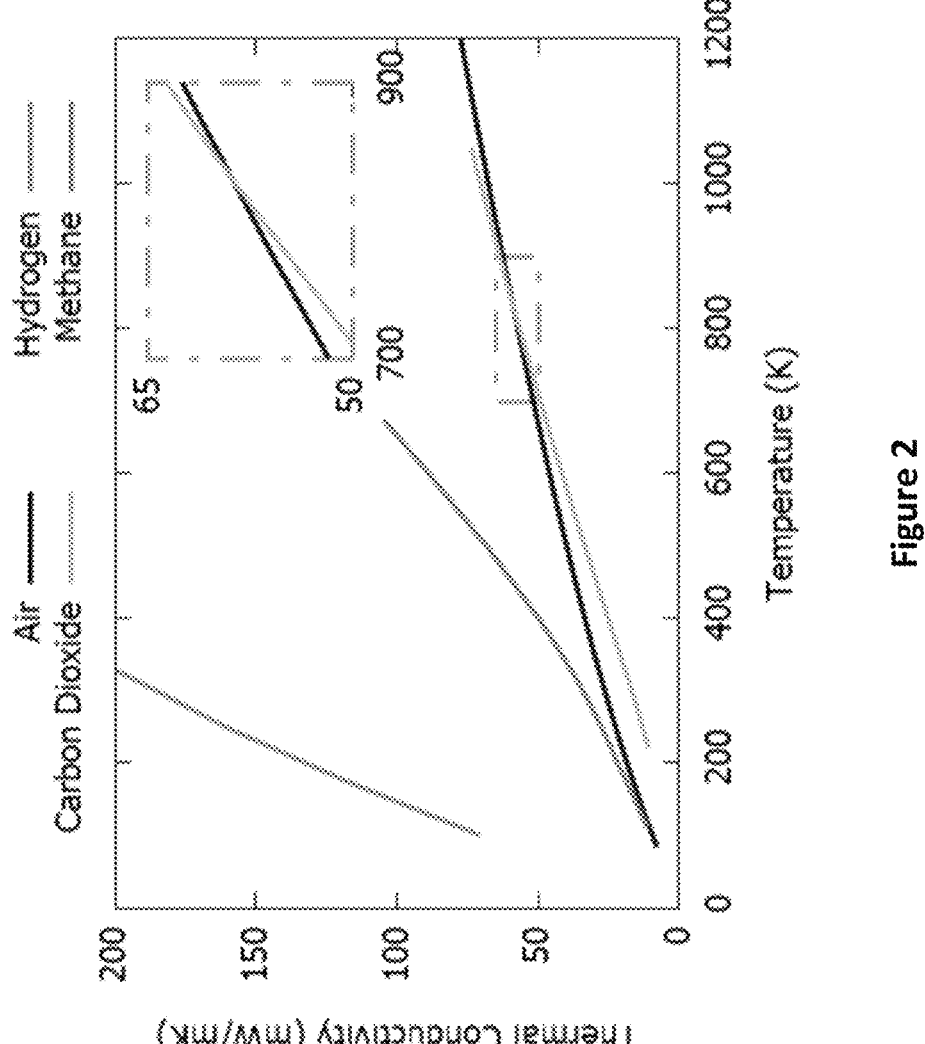
FIG. 2 is a diagram of the thermal conductivity of some example gases as a function of the temperature.

FIG. 2 is a diagram of the thermal conductivity of some example gases as a function of the temperature, e.g. the temperature of the heating element of the thermal conductivity fluid sensor. FIG. 2 shows how the thermal conductivity of the example gases varies with temperature.

Figure 3:
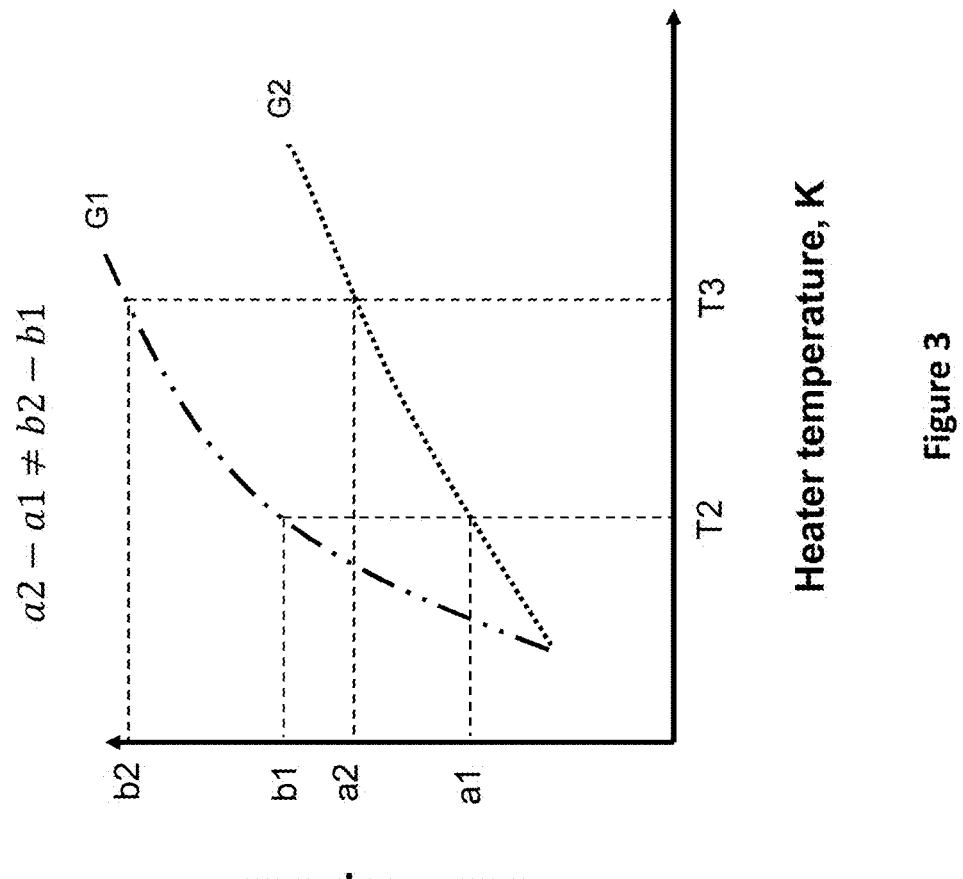
FIG. 3 is a diagram showing the variation of the heating element response of a thermal conductivity fluid sensor towards two generic example gases.

FIG. 3 is a diagram showing the variation of the heater response of a thermal conductivity fluid sensor toward two generic example gases, gas 1 (G1) and gas 2 (G2). As shown in FIG. 3, at temperature T1 and T2, at which sensor readings are taken, the response of the sensor for the two example gases varies differently and this difference may be used to decouple the sensor response towards G1 and towards G2, for example to determine the contribution of G2 to the readings.

It will be understood that obtaining readings at additional temperature values (i.e. more than two as shown in the example of FIG. 3), will in general enable improved accuracy in the calculation of the contribution of G2.

Once the contribution of G2 has been calculated, the heating element may be set at a nominal bias temperature, for example, a bias temperature which has been identified as the temperature at which the sensor has the highest response for G1, in the range of operational temperatures. A new reading of the mixture is taken and G1 is determined by subtracting the contribution of G2 at the nominal bias temperature.

Alternatively, the heating element may be set at a nominal bias temperature, for example, a bias temperature which has been identified as the temperature at which the sensor shows the largest difference in response between G1 and G2 (the response for G1 being the highest of the two), in the range of operational temperatures, a new reading of the mixture is taken and G1 is determined by subtracting the contribution of G2 at the nominal bias temperature.

It will be understood that any other suitable nominal bias temperature may be chosen.

For example, G1 may be $H_2$ and G2 may be humidity. In this example $H_2$ is a target gas and humidity is a parasitic.

Figure 4:
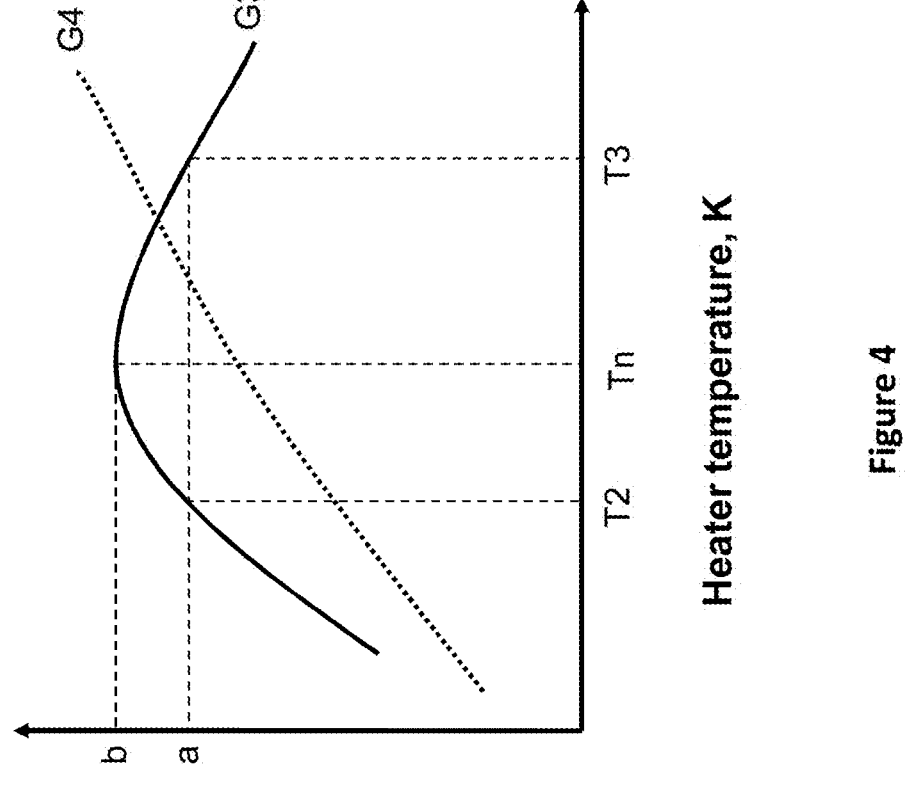
FIG. 4 shows the sensitivity of a thermal conductivity fluid sensor towards two further example gases.

FIG. 4 shows the sensitivity of a thermal conductivity fluid sensor towards two example gases, gas 3 (G3) and gas 4 (G4), as a function of the temperature of the heating element. The sensitivity towards G3 goes through a maximum in the range of operational temperatures of the sensor.

In these cases, the controller may be configured to:

at (a), set the heating element at a first temperature bias T1, of the two or more temperature bias, which is below the nominal temperature bias (which may be, for example Tn in FIG. 4) and at a second temperature bias T2 of the two or more temperature bias which is above the nominal temperature bias Tn. The controller may be further configured to, at (c)., determine the signal produced by the second component, G4, based on the differential signal of two of the readings of (b). Since at T1 and T2 the sensitivity of the sensor towards G3 is the same, the contribution of G3 to the readings may be cancelled out and the contribution of G4 may be obtained.

It will be understood that a differential signal is a signal that may be obtained by calculating the difference between two readings. The two readings may be taken at different points in time, or the two readings may be taken simultaneously (real-time differential), as it will be explained below.

As shown in FIG. 4, if G3 were in a mixture with G4, the differential of the readings taken at any two temperature values, T1 and T2, where T1 is lower than Tn and T2 is higher than Tn (where Tn is the temperature of highest sensitivity towards G3 in the range of operational temperatures), and the sensitivity towards G3 is the same at T1 and T2, would allow to cancel out the contribution of G3 to the readings taken for a mixture comprising G3 and G4 at T1 and T2. In this way, the contribution of G4 may be readily obtained and used to calculate the contribution of G3 to the readings taken for a mixture comprising G3 and G4 at T1 and T2. By getting more readings at Tx and Ty pairs at which the sensor shows the same sensitivity towards G3, a calibration curve may be obtained allowing to extrapolate the contribution of G4 at Tn, for example where the sensitivity towards G3 is maximum in the range of operational temperatures. Taking a reading at the temperature of maximum sensitivity towards G3 allows to obtain a more accurate result for G3. For example, G3 may be $CO_2$ and G4 may be humidity. In this example $CO_2$ is a target gas and humidity is a parasitic.

Having the contribution of G1 and G2 (or G3 and G4) measured or calculated through readings collected using just one feature, the heating element, of the thermal conductivity sensor allows to increase the accuracy of the final values obtained for either gas contribution because any variation due to the use of a different technology and/or due to conducting the measurements in different environments, e.g. with different temperature or pressure or flow conditions, are removed. Besides, since both gases are detected at the same point in space, any local variations of the composition of the mixture is prevented from affecting the measurements.

The present inventors have observed that the thermal transport behaviour changes from one gas (or, a fluid) to another when the first heating element is in a thermal transient time period (e.g. while the temperature of the heating element changes from a first temperature to a second temperature). This is reflected in the invention described in the present disclosure.

As discussed, the thermal conductivity fluid sensor according to the present disclosure, comprises a controller which is configured to take a reading during the thermal transient time period, e.g. the heating up period, of the heating element exposed to the measured atmosphere, before it has reached the steady-state at a set temperature. Taking a reading (or multiple readings) during a transient period of time will provide information that relates to thermal diffusivity characteristics of each component of the gas mixture (rather than thermal conductivity which is used for detecting a gas once the heating element has reached the thermal steady-state). This will provide information for input to the algorithms to de-couple multiple gases that are mixed together due to the transient nature of thermal transport behaving differently to gases.

Figure 5:
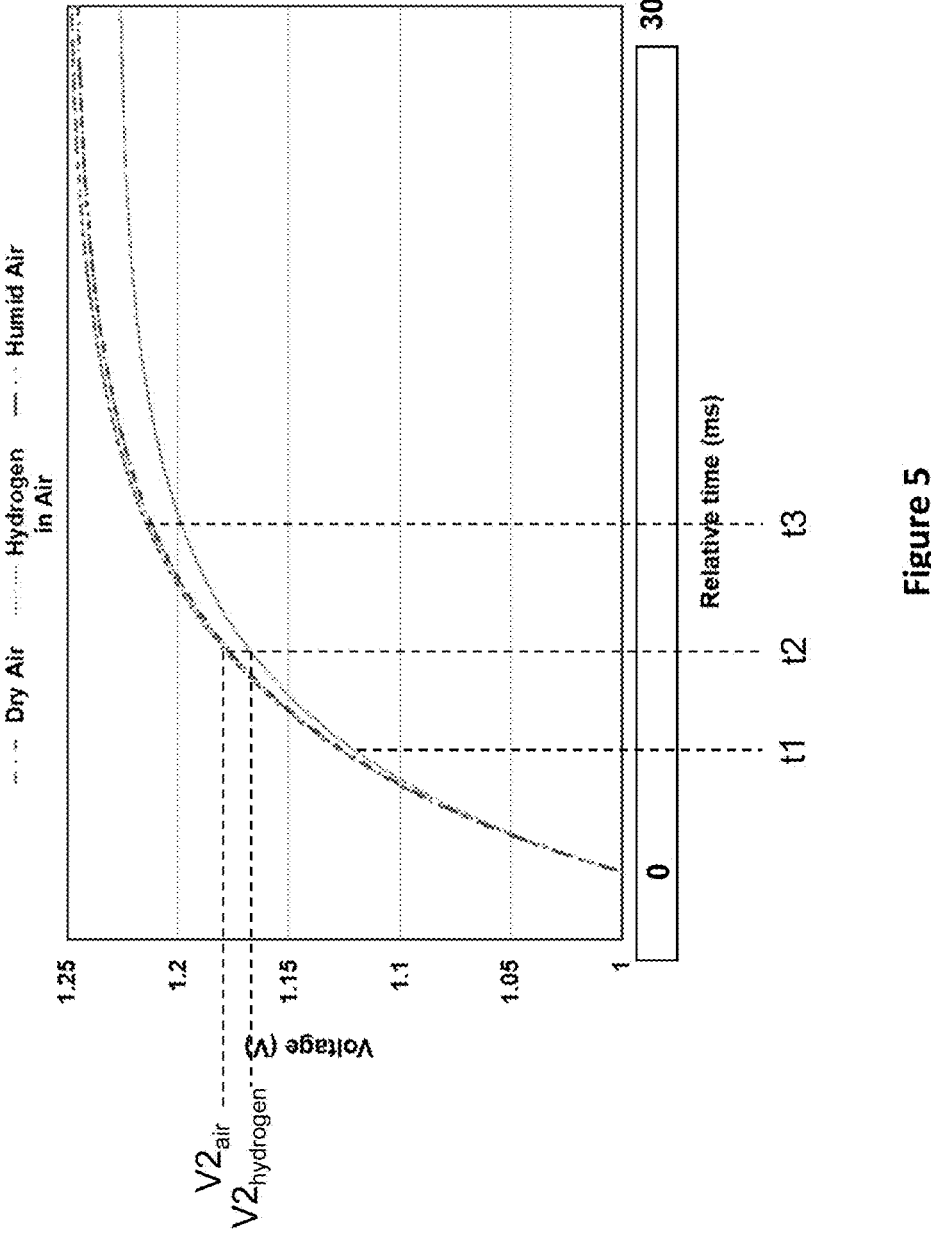
FIG. 5 illustrates an example of a change in heating element voltage over time from turning on for a heating element in fluid communication with environments comprising three different gases or gas mixtures.

FIG. 5 illustrates an example of a change in heating element voltage over time from turning on the heating element in fluid communication with environments comprising three different gas mixtures: dry air, hydrogen in air, and humid air. It will be understood that the voltage data refer to the voltage applied to the heating element to reach a predetermined temperature at a predetermined rate and may be converted in values of the temperature of the heating element as a function of time. Voltage data are, in general, raw data.

As shown in FIG. 5, at a point in time t after the heating element is turned on, a measurement can be taken (e.g. at t2). The response of the heating element (e.g. measured heating element voltage or temperature) is different depending on the composition of the gas mixture present, and is determined by the thermal diffusivity of the gas mixture (e.g. V2air and V2hydrogen). Thus, the thermal diffusivity of the gas mixture can be determined from the response of the heating element, which may provide alternative or different information on the composition of the gas mixture, with respect to the information provided by a thermal conductivity measurement.

Some examples of thermal diffusivities of various gases and gas mixtures are shown in the table below:

TABLE

Thermal diffusivities of various gases and gas mixtures.

| Gas | Temperature (K) | Pressure (atm) | Thermal diffusivity $(mm^2/s)$ |
|---|---|---|---|
| Dry air | 300 | 1 | 19 |
| Water vapor | 380 | 1 | 20.4 |
| Hydrogen | 300 | 1 | 160 |
| Carbon dioxide | 300 | 1 | 11 |
| Helium | 300 | 1 | 190 |
| Nitrogen | 300 | 1 | 22 |
| Argon | 300 | 1 | 22 |

For a gas mixture comprising a first component and a second component, temperature-dependent thermal diffusivity data may be combined with temperature-dependent thermal conductivity data to determine the contribution of the two components of the gas mixture to a temperature sensitive thermal transport property of the gas mixture.

The controller 110 of the sensor of the present disclosure is, therefore configured to control a temperature of the first heating element such that the temperature of the first heating element changes from a first temperature to a second temperature over a first transient time period;

obtain a first reading indicative of a first thermal transport property of the gas mixture during the first transient time period;

obtain a second reading indicative of second thermal transport property of the gas mixture when the first heating element is at the second temperature; and determine, based on the first reading and the second reading, a concentration of a the first component of the gas mixture.

Figure 6:
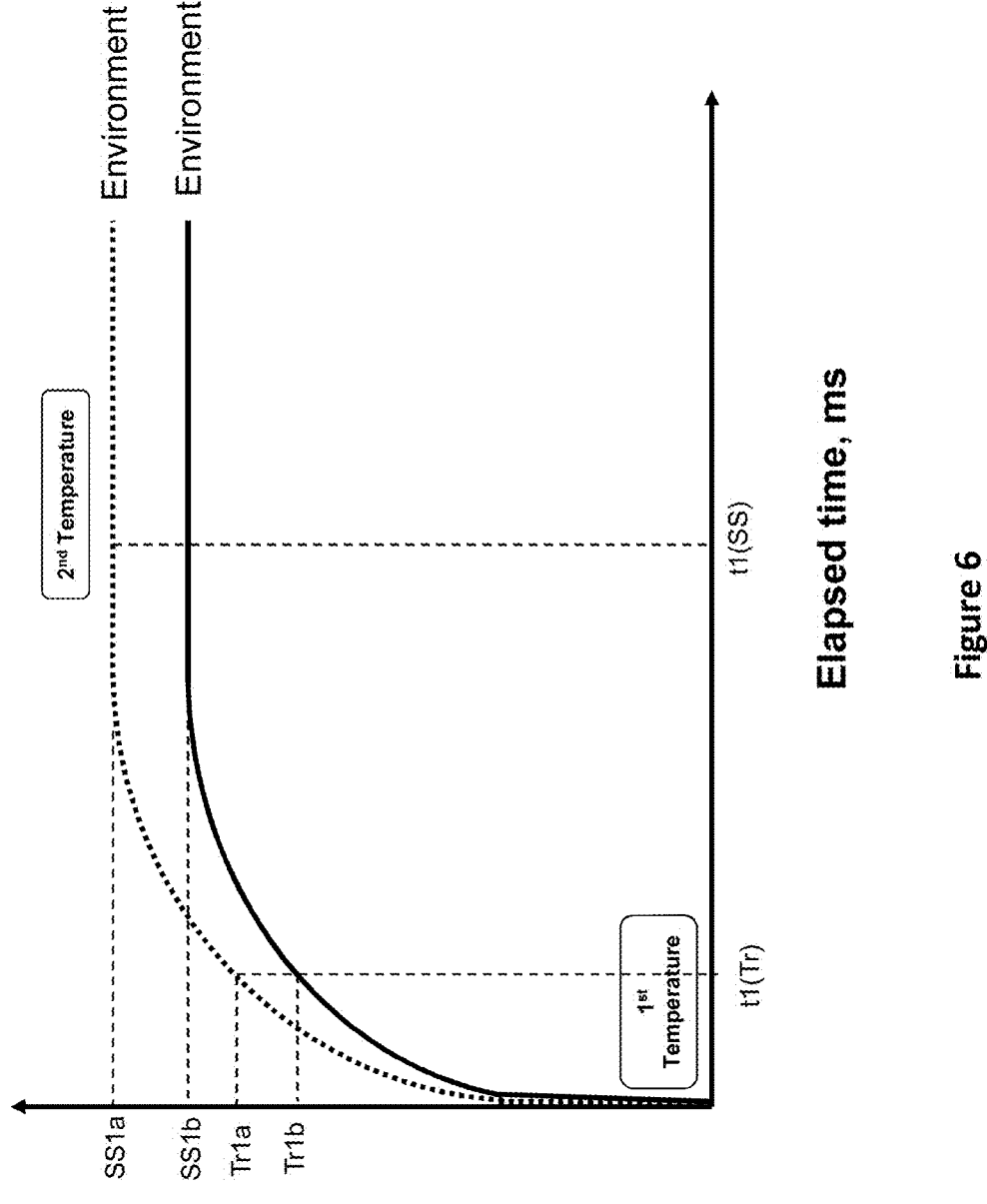
FIG. 6 illustrates an example of a variation of a heating element temperature with time for two different environments.

FIG. 6 shows how a thermal conductivity fluid sensor provides a different reading for two different environments ("Environment a" and "Environment b") to which the first heating element 105 may be exposed, both during the transient time period, e.g. values Tr1a and Tr1b at time t1(Tr), while the temperature of the heating element is raised from a first temperature to a second temperature, and when the heating element has reached a the steady state at the second temperature, e.g. values SS1a and SS1b at t1(SS). FIG. 6 shows a case where the second temperature is higher than the first temperature. In other cases, the second temperature may be lower than the first temperature.

As shown in the example illustrated in FIG. 6, the actual temperature reached by the heating element 105 when the set temperature is the second temperature, may be different for a given input (e.g. heating element current or power which would make the heating element reach the second temperature as its actual temperature, if the heating element were in the calibration environment) depending on the environment in which the heating element is located. This is due to the heat loss from the heating element towards the environment which depend on the nature and composition of the environment. A reading of the heating element temperature (at a steady state, e.g. at time t1(SS)), therefore, provides information about that environment. In some examples, the heating element may be controlled such that the temperature reached by the heating element (the second temperature) is always the same independent of the environment. In such examples, a reading may comprise a current, voltage, and/or power provided to the heating element in order for the heating element to reach that (second) temperature. Since in such examples the current, voltage, and/or power needed to reach a given temperature will change according to the environment, a reading of one or more of these properties is also informative of the composition of the environment.

Figure 7:
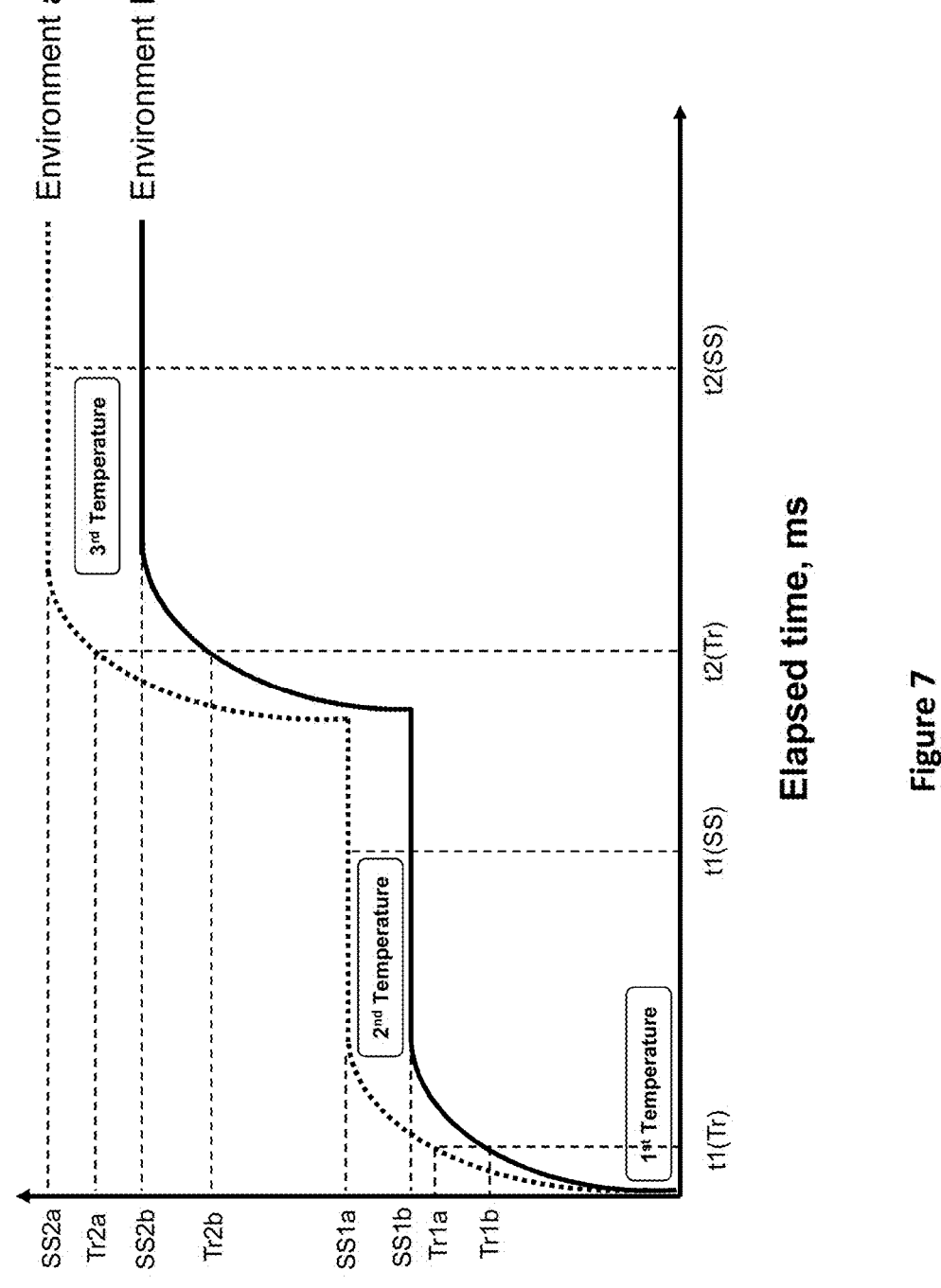
FIG. 7 illustrates an example of a variation of a heating element temperature with time in accordance with some examples described herein.

FIG. 7 shows that the difference in response of the heating element changes with the temperature in different ways at different temperature values for different gases or gas mixtures. Therefore, to obtain more accurate readings to allow the decoupling of the contributions of two components to a reading at a nominal bias temperature, the controller may further change the temperature of the heating element from the second temperature to a third temperature and obtain a further reading during the new transient time period and/or when the heating element is at the third temperature.

FIG. 7 shows a case where the third temperature is higher than the second temperature. In other cases, the third temperature may be lower than the second temperature.

Figure 8:
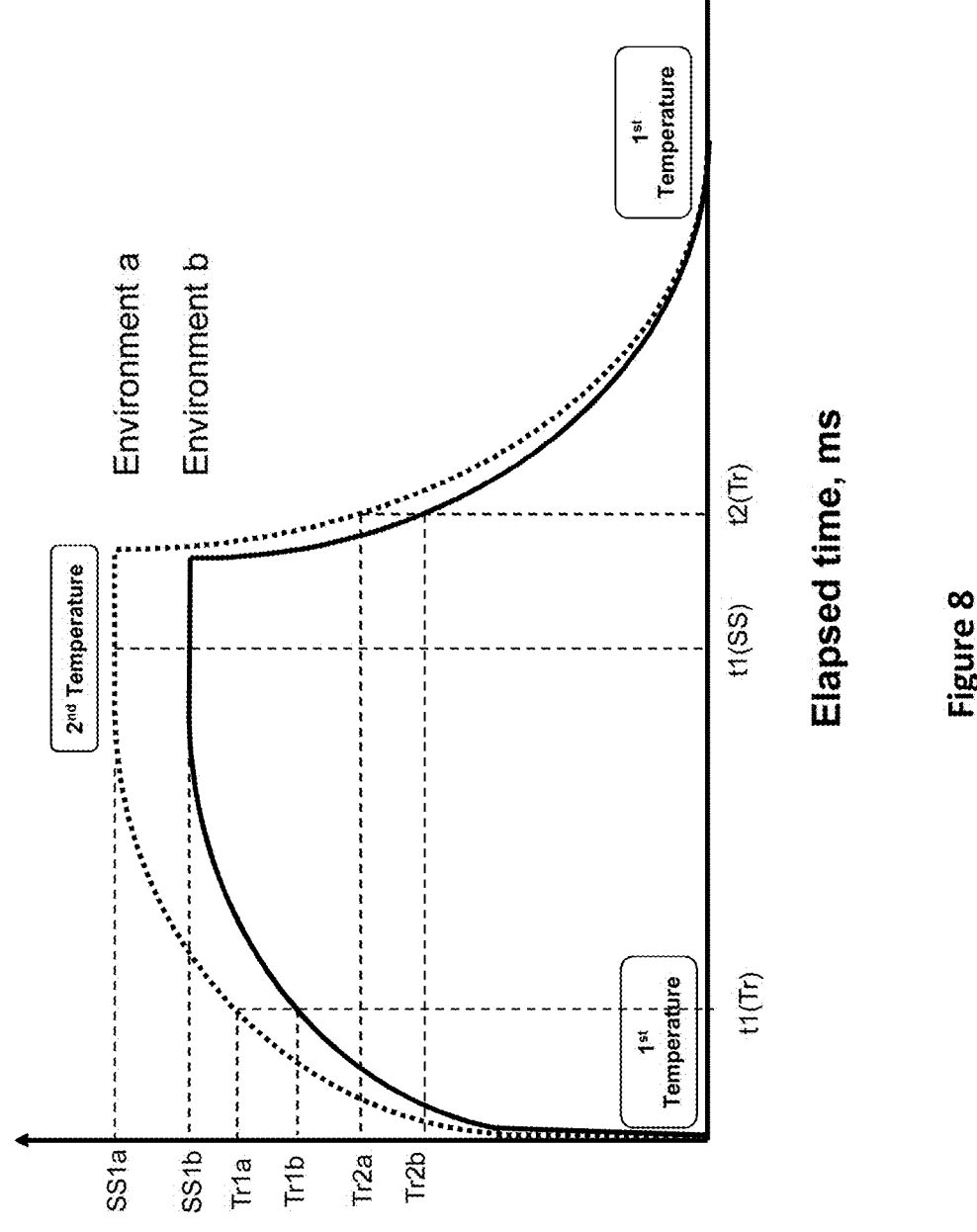
FIG. 8 illustrates a further example of a variation of a heating element temperature with time in accordance with some examples described herein.

FIG. 8 further shows a case where the third temperature is the same as the first temperature and the thermal transport behaviour of the two gases or gas mixture (Environment a and Environment b) during the heating transient time period is different from the behaviour of the two environments during the cooling transient time period.

The controller may be configured to take readings while the heating element cools down from a second temperature to a first temperature, for example ambient temperature. This may provide further information related to the fact that the temperature constant, i.e. the change of temperature in the unit of time, for a single component may be different when the component is heated from when the component is cooled, the rate of cooling being typically higher. The controller may further be configured to take one or more readings during the heating transient period, at the steady-state and during the cooling transient period.

The controller may be configured to take single measurements in time during the heating period of the heating element, or it can take multiple readings and determine the integral of the slope of the curve of the temperature as a function of time.

The information which may be extracted from such transient readings may be used alone, e.g. for calibrating the sensor, or it may be combined with the readings taken at the steady state.

Taking readings during the transient period allows to gain more information on the single components of the mixture and allows optimising the on time of the thermal conductivity fluid sensor, ultimately making it more energy efficient and flexible in terms of modes of operation.

In some examples, the controller may be configured to synchronize a clock with turn-on of the heating element to enable readings at a very precise time.

Multiple readings may be taken along a transient time period of the heating element. These may be integrated for the area under the curve or taken as standalone responses.

Figure 9A:
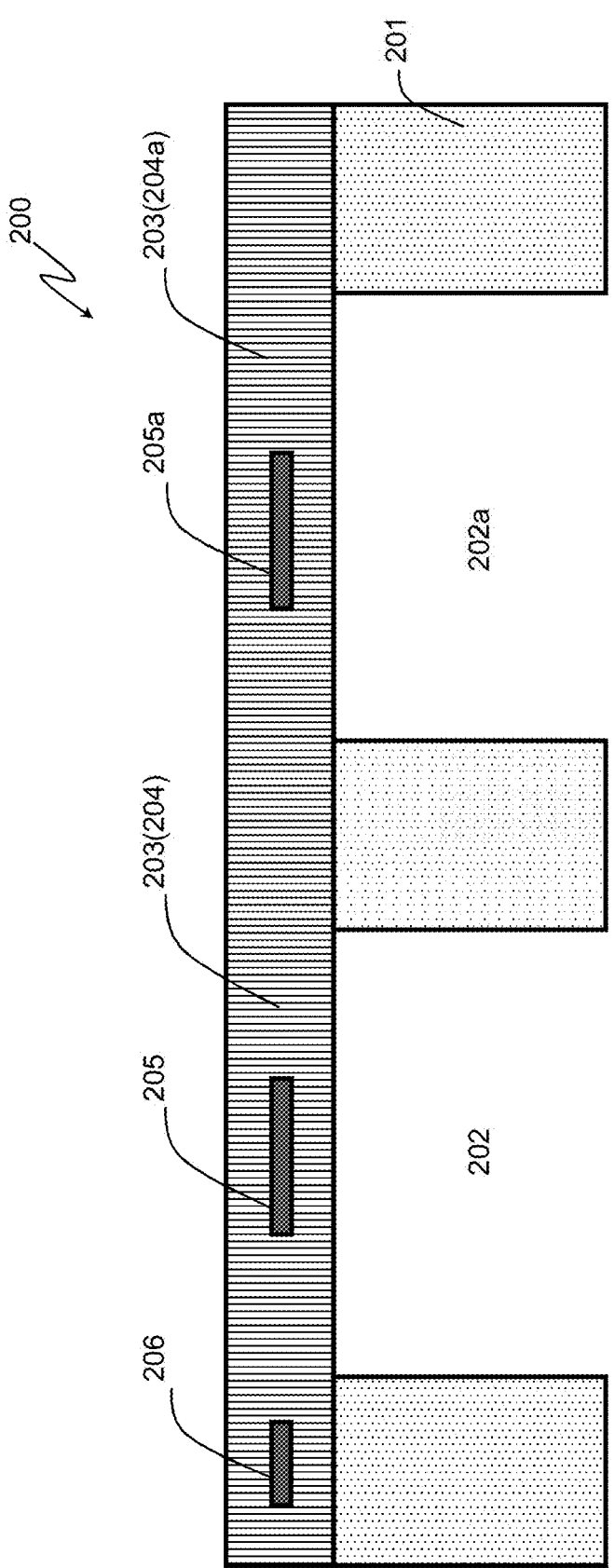
FIGS. 9A to 9C illustrate examples of a thermal conductivity fluid sensor comprising a second heating element.
Figure 9B:
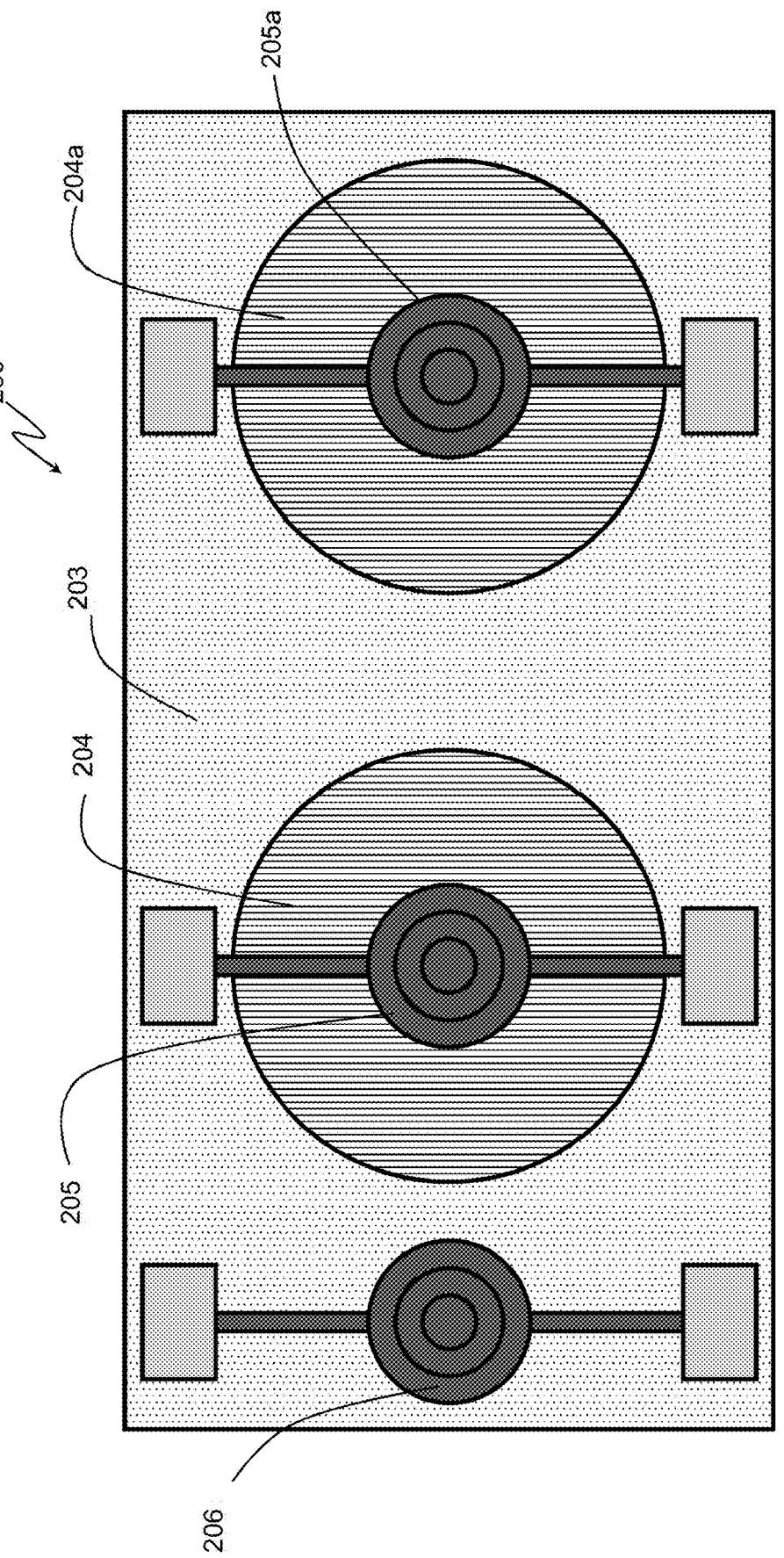

In other examples, as shown in FIGS. 9A and 9B, the thermal conductivity fluid sensor 200 comprises a second membrane 204a provided with a second heating element 205a. The second heating element 205a is thermally insulated from the first heating element 205. In these cases, the controller (not shown) may be configured to control a temperature of the second heating element 205a such that the temperature of the second heating element 205a changes from a fourth temperature to a fifth temperature over a further first transient time period, the fifth temperature being different from the second temperature; and obtain a fourth reading indicative of a fourth thermal transport property of the gas mixture during the further first transient time period or when the heating element is at the fifth temperature.

Preferably, the first transient period and the further first transient period are substantially of the same length so that the readings obtained using the first heating element 205 and the second heating element 205a are obtained substantially at the same time.

In other examples, the first transient period and the further first transient period may be of different lengths so that they overlap, at least in part.

In this way, the contribution of the two gases can be determined in significantly less time as readings at different temperature values may be taken simultaneously or almost simultaneously.

Figure 9C:
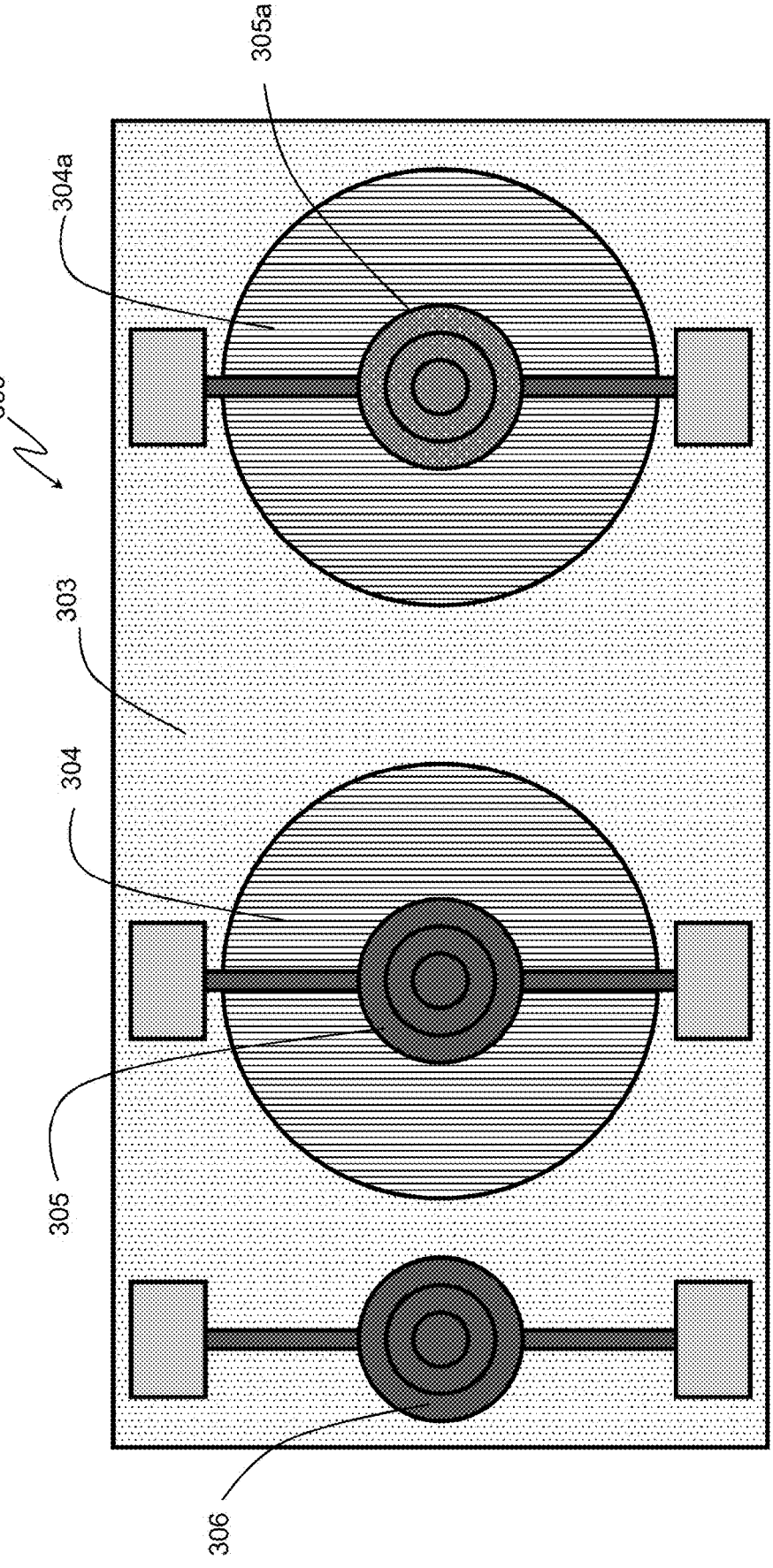

In some examples, as depicted in FIG. 9B, the first heating element 205 and the second heating element 205a may be identical, e.g. in shape size and/or material. In other examples, as depicted in FIG. 9C, the first heating element 305 and the second heating element 305a may be different from each other. For example, the first heating element 305 and the second heating element 305a may have different structural compositions, which may include comprising different materials and/or having different dimensions such that the heating elements may be optimised for different temperature ranges. In some examples, one of the heating elements, e.g. 305, may have a lower operational temperature range and the other, e.g. 305a, may have a higher operational temperature range. In this way, the overall temperature range of the thermal conductivity fluid sensor 300 may be extended to provide more flexibility, so that the sensor may be suitable for the detection of a wider range of fluid components.

Figure 10A:
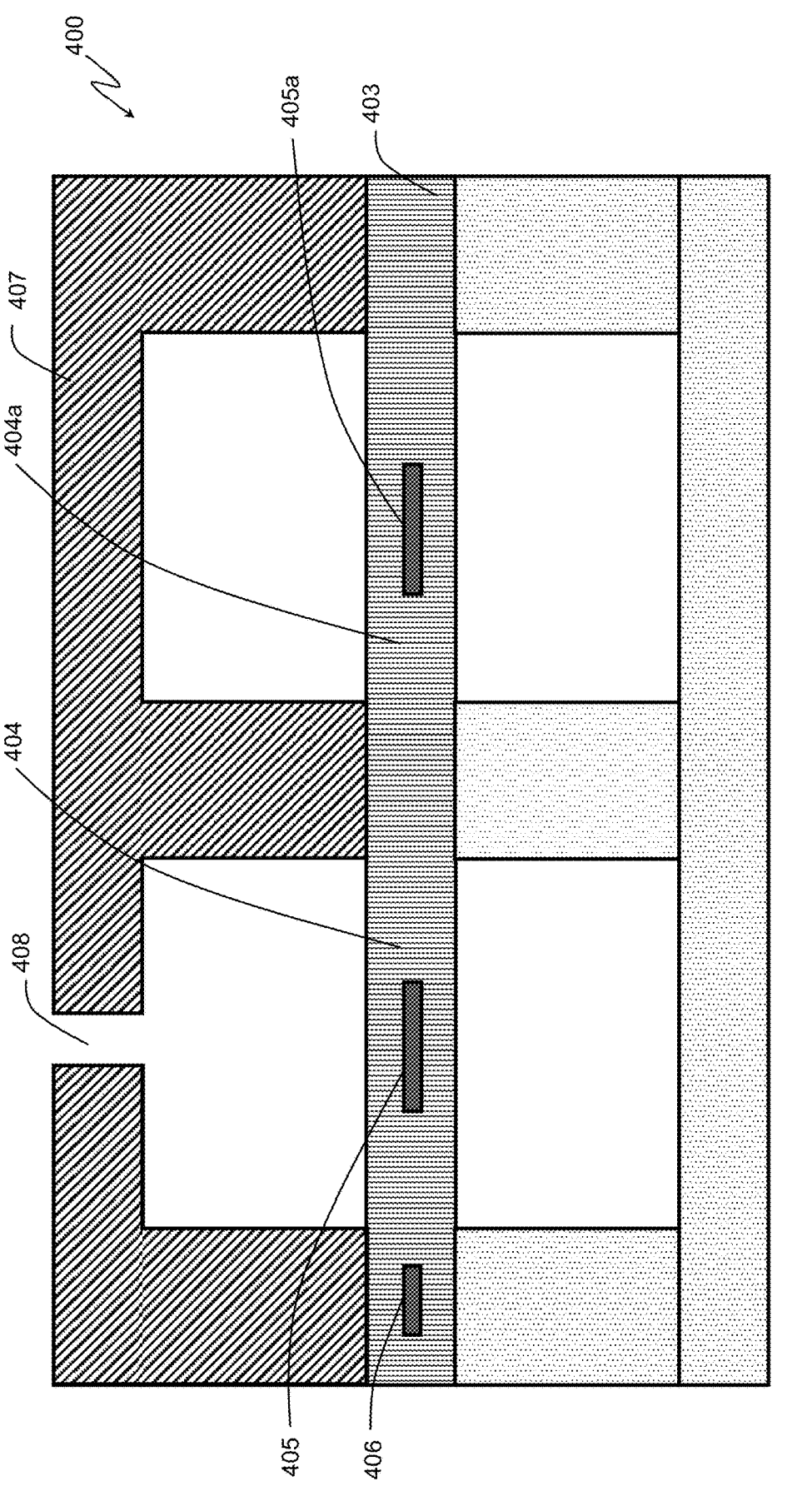
FIGS. 10A to 10C illustrate examples of a thermal conductivity fluid sensor provided with a cap layer.
Figure 10B:
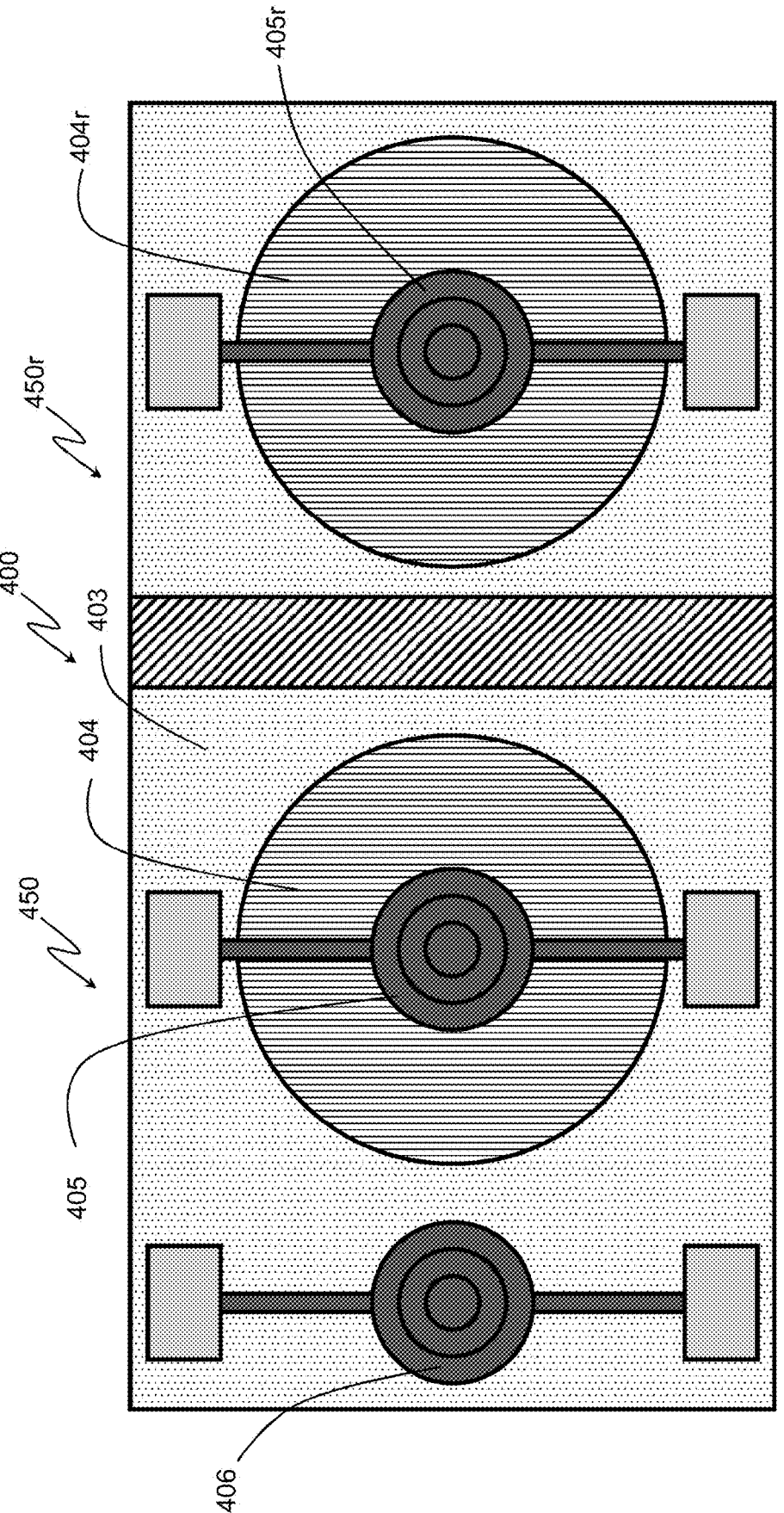
Figure 10C:
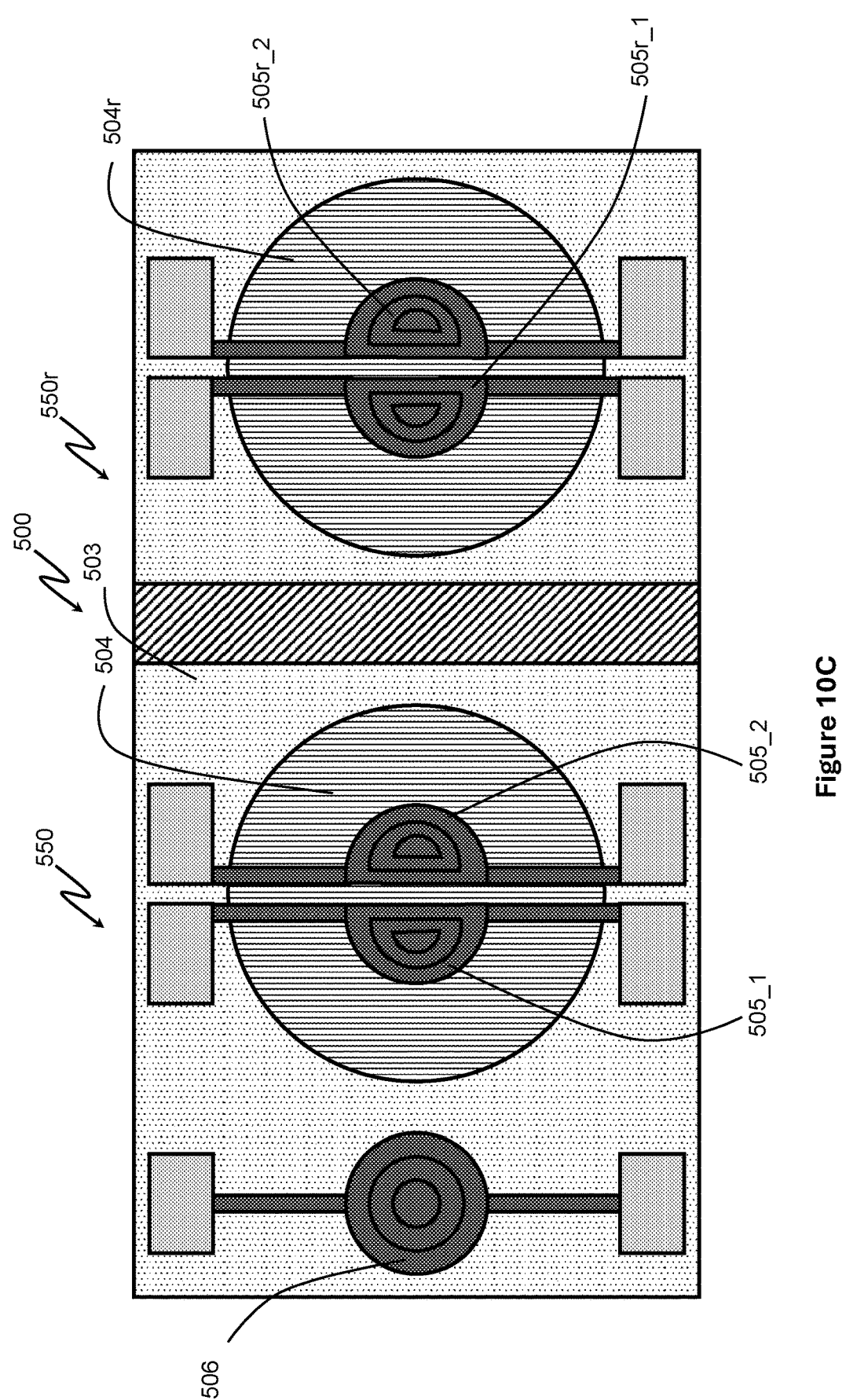

In further examples, as shown in FIGS. 10A to 10C, the thermal conductivity fluid sensor 400 is provided with a cap (or lid) 407, also referred to as a cap layer, above the first and second membranes 404, 404r. The portion of the cap 407 above the first membrane 404 is provided with a hole 408 which allows the first membrane 404 to be in contact with the external environment (or atmosphere) where the gas mixture is present. This may be defined as a measured atmosphere. The portion of the cap 407 above the second membrane 404r, on the other hand, is closed so as to isolate the second membrane 404r from the measured atmosphere. In some cases, the cap 407 may seal the second membrane 404r. The space between the second membrane 404r and the cap 407 may be under vacuum or it may contain a controlled atmosphere, for example comprising nitrogen, dry air or the like. This may be defined as a reference atmosphere.

In this case, the controller (not shown) may be configured to set the temperature of the first 405 and second 405r heating element at substantially the same values at substantially the same time, so that separate, corresponding, readings may be taken at the same temperature values and at the same time, but in the presence of a different atmosphere, the first heating element 405 being in contact with the measured atmosphere, and the second heating element 405r, which, as in this case, may take the function of a reference heating element, being exposed to a reference atmosphere.

In such cases, the controller may be configured to take readings of the measured atmosphere and of the reference atmosphere at the same time and at the same set temperature of the heating elements 405, 405r so as to record an instantaneous differential response between the measured atmosphere and the reference atmosphere.

This may be repeated in the steady state, at a plurality of temperature values, and/or at the same time during one or more transition time periods, as appropriate. The differential response obtained in this configuration of the controller is not affected by a variation in the ambient conditions, as any effect caused by, for example, a variation of the ambient temperature is cancelled out when obtaining a differential reading between the reading obtained using the first heating element and the reading obtained using the second heating element at the same time and/or set temperature. In this way the readings of the measured atmosphere will be more accurate. Those readings may be used to determine the contributions of the first and second component as described above in connection with thermal conductivity fluid sensors 100 with only one membrane 104 and one heating element 105, one example of which is shown in FIGS. 1A and 1B.

The thermal conductivity fluid sensor 400 may still be provided with a further temperature sensor 406, for example an ambient temperature sensor, which may be used for compensating for secondary effects linked to the environment temperature, which may be due to manufacturing tolerances which may introduce thermal mismatches from one component to the other of a device, so further increasing the accuracy of the readings, and/or to independently measure the ambient temperature.

In some examples, one of which is depicted in FIG. 10C, the first heating element, and the second heating element (when present) may comprise two separate heating elements or semi-elements 505_1, 505_2, 505r_1, 505r_2, respectively. Those semi-elements may be connected as part of a circuit, such as a Wheatstone bridge, to increase the sensitivity of the thermal conductivity fluid sensor 500.

In cases where only one membrane is present and in those where a second membrane is also present, such as in the examples shown in FIGS. 9B and 9C, where the membrane and the second membrane can be independently heated at different temperatures, the heating element may still be formed of two semi-elements and each couple of semi-elements may be part of a Wheatstone bridge together with two fixed reference resistors, as shown in FIG. 11A. This configuration allows to obtain differential measurements so increasing the sensitivity of the fluid sensor, compared to fluid sensors having only one heating element as a single (or unitary) element.

In cases where two membranes are present, such as in the examples shown in FIGS. 10B, and they are heated at the same temperature at the same time, but are exposed to different environments (e.g. a measured atmosphere and a reference atmosphere), the two couples of semi-elements may be connected in the same Wheatstone bridge as shown in FIG. 11B. This configuration allows to obtain differential measurements which are double in module with respect to those that may be obtained with the configuration shown in FIG. 11A so further increasing the sensitivity of the fluid sensor.

Figure 12:
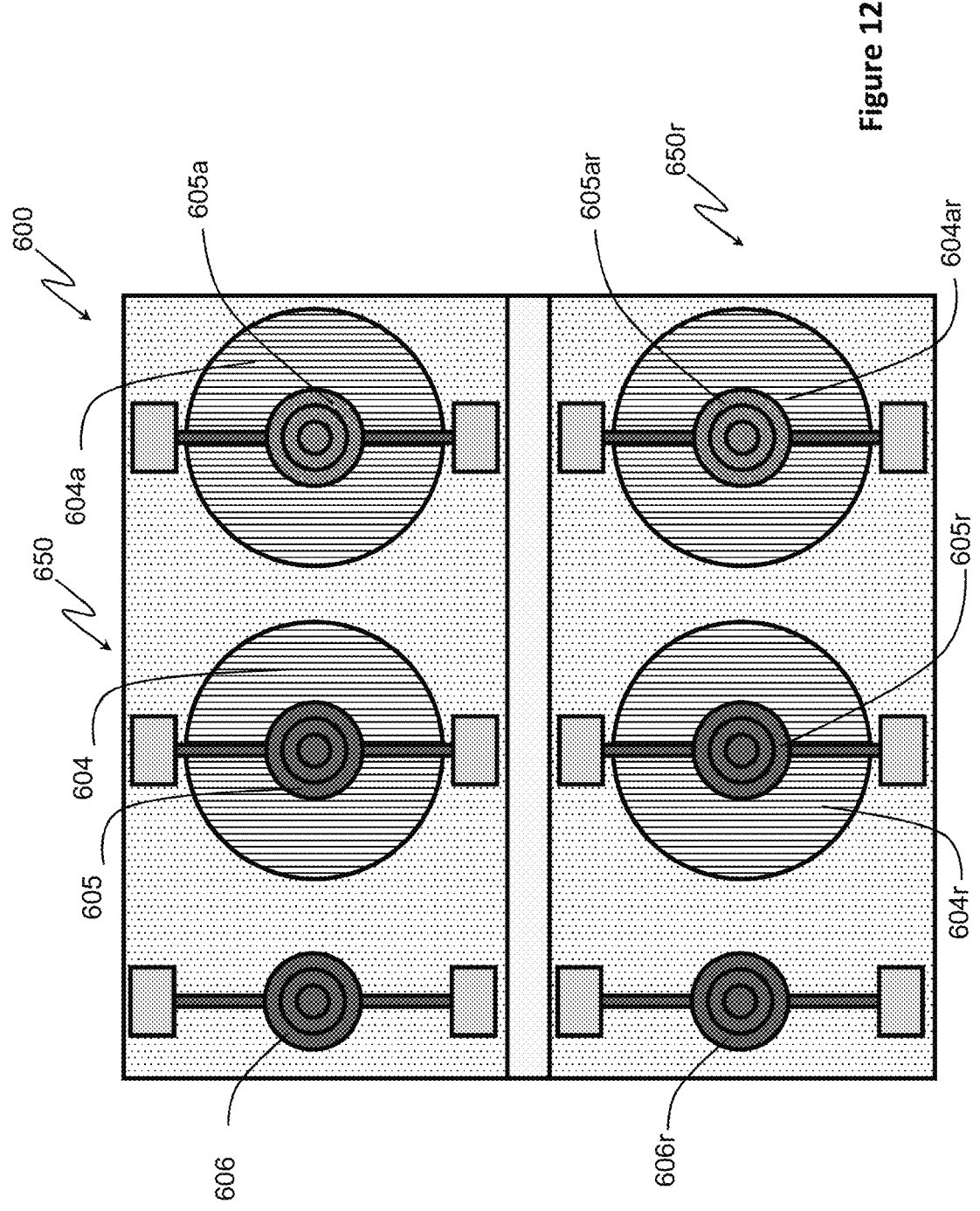
FIG. 12 illustrates an example of a thermal conductivity fluid sensor comprising a sensing section and a reference section.

In some further examples, the devices show in FIGS. 9 and 10 may be combined in a single device, as shown in FIG. 12, depicting a thermal conductivity fluid sensor 600 comprising a sensing section 650, exposed to the measured atmosphere, and a reference section 650r, exposed to a reference atmosphere, both provided with a first membrane 604, 604r and a second membrane 604a, 604ar and respective heating elements 605, 605r, 605a, 605ar.

In this implementation, the sensing section 650 is exposed to the measured atmosphere and works as described in relation to FIGS. 9A to 9C, with the first and second heating elements 605, 605a capable of being set at different temperatures independently of each other. The first and second heating elements 605 and 605a may be identical to, or different from, each other, as discussed above.

Differently from the examples of FIGS. 9A to 9C, the first and second heating elements 605, 605a of the sensing section 650 are each connected to a corresponding heating element 605r, 605ar in the reference section 650r. Each pair formed of a heating element 605 or 605a of the sensing section 650 and a respective heating element 605r, 605ar of the reference section 650r may be heated independently at a different temperature, while the heating elements of the same pair (one pair comprising heating elements 605 and 605r and the other comprising heating elements 605a, 605ar) are heated at the same temperature, at the same time. The heating elements of each pair may be identical to each other. In this way, each reading is corrected for the contributions of the ambient conditions, such as the ambient temperature and the thermal conductivity fluid sensor provides readings of improved accuracy in reduced time.

In any of the above described thermal conductivity fluid sensors, the controller may comprise a memory element that is able to store the information during a calibration mode and/or sensing mode (i.e. when obtaining readings in the presence of the measured atmosphere) and use said information to compute the differential signal or the reference signal. The controller may be part of an ASIC circuit. The ASIC circuit may be provided in the same chip (monolithically integrated) as the membrane(s) or in a separate chip but in the same package (system in package) or in a separate package.

The thermal conductivity fluid sensor of the disclosure may be manufactured using any suitable method known in the art, for example, but not limited to, a MEMS process and/or a CMOS process.

FIG. 13 illustrates an example of a method 1100 for determining a first concentration of a component of a (gas) mixture. The method 1100 may be carried out, e.g., using any of the example thermal conductivity fluid sensors 100, 200, 300, 400, 500, 600, described herein. For example, at least part of the method 1100 may be carried out by the controller 110.

At S1102, the method 1100 comprises changing a temperature of a first heating element from a first temperature to a second temperature over a first transient time period. For example, the first heating element may be a heating element 105, 205, 305, 405, 505, 605 described herein.

At S1104, the method 1100 comprises obtaining a first reading indicative of a first thermal transport property of the (gas) mixture during the first transient time period. The first reading may comprise, for example, a temperature reading of the gas (e.g. of the heating element) and/or a voltage reading of the heating element. The first thermal transport property may be a thermal diffusivity of the gas mixture.

At S1106, the method 1100 comprises obtaining a second reading indicative of a second thermal transport property of the (gas) mixture when the first heating element is at the second temperature. The second reading may comprise, for example, a temperature reading of the gas (e.g. of the heating element) and/or a voltage reading of the heating element. The second thermal transport property may be a thermal conductivity of the gas mixture.

At S1108, the method 1100 comprises determining, based on the first reading and the second reading, a concentration of the first component of the (gas) mixture. The concentration of the first component of the gas mixture may be determined according to any suitable method, including any of the methods described herein.

Even though the present disclosure refers to gas mixtures and gas components, it will be appreciated that the invention of the disclosure may be applied to fluid mixtures and fluid components in general, including gases and liquids.

Although the disclosure has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the disclosure, whether alone or in any appropriate combination with any other feature disclosed or illustrated herein.

The invention claimed is:

1. A thermal conductivity fluid sensor for detecting a first component of a mixture, the thermal conductivity fluid sensor comprising:
a first heating element; and
a controller, the controller configured to:
control a temperature of the first heating element such that the temperature of the first heating element changes from a first temperature to a second temperature over a first transient time period;
obtain a first reading indicative of a first thermal transport property of the mixture during the first transient time period;
obtain a second reading indicative of second thermal transport property of the mixture when the first heating element is at the second temperature; and
determine, based on the first reading and the second reading, a concentration of the first component of the mixture.

2. The thermal conductivity fluid sensor according to claim 1, wherein the controller is configured to obtain the first reading at a predetermined time during the first transient time period.

3. The thermal conductivity fluid sensor according to claim 1, wherein the controller is configured to:
control the temperature of the first heating element such that the temperature of the first heating element changes from the second temperature to a third temperature over a second transient time period;
obtain a third reading indicative of a third thermal transport property of the mixture during the second transient time period or when the heating element is at the third temperature; and
determine, based additionally on the third reading, the concentration of the component of the mixture.

4. The thermal conductivity fluid sensor according to claim 1, comprising a second heating element thermally insulated from the first heating element, the second heating element being located in a sealed chamber, the sealed chamber containing a reference environment;
wherein the controller is configured to:
control a temperature of the second heating element such that the temperature of the second heating element changes from the first temperature to the second temperature over the first transient time period;
obtain a first reference reading indicative of a first thermal transport property of the reference environment during the first transient time period;
obtain a second reference reading indicative of a second thermal transport property of the reference environment when the second heating element is at the second temperature; and
determine the concentration of the component of the mixture based additionally on the first reference reading and the second reference reading.

5. The thermal conductivity fluid sensor according to claim 1, comprising a second heating element thermally insulated from the first heating element, wherein the controller is configured to:
control a temperature of the second heating element such that the temperature of the second heating element changes from a fourth temperature to a fifth temperature over a further first transient time period, the fifth temperature being different from the second temperature; and
obtain a fourth reading indicative of a fourth thermal transport property of the mixture during the first transient time period or when the heating element is in steady state at the fifth temperature.

6. The thermal conductivity fluid sensor according to claim 5, wherein the first heating element has a first structural composition, and wherein the second heating element has a second structural composition different from the first structural composition.

7. The thermal conductivity fluid sensor according to claim 4, comprising a cap layer, the cap layer having a first cap portion disposed over the first heating element, and a second cap portion disposed over the second heating element;
wherein the first cap portion is provided with an opening such that the first heating element is in fluid communication with a measured atmosphere.

8. The thermal conductivity fluid sensor according to claim 7, wherein the second cap portion forms part of the sealed chamber.

9. The thermal conductivity fluid sensor according to claim 1, wherein the first heating element comprises two heating element portions.

10. The thermal conductivity fluid sensor according to claim 1, comprising an ambient temperature sensor.

11. A method for determining a concentration of a component of a mixture, the method comprising:
changing a temperature of a first heating element from a first temperature to a second temperature over a first transient time period;
obtaining a first reading indicative of a first thermal transport property of the mixture during the first transient time period;
obtaining a second reading indicative of a second thermal transport property of the mixture when the first heating element is at the second temperature; and
determining, based on the first reading and the second reading, a concentration of the component of the mixture.

12. The method according to claim 11, comprising obtaining the first reading at a predetermined time during the first transient time period.

13. A method according to claim 11, wherein the second temperature is higher than the first temperature.

14. A method according to claim 11, wherein the second temperature is lower than the first temperature.

15. The method according to claim 11, further comprising:
changing the temperature of the first heating element from the second temperature to a third temperature over a second transient time period;
obtaining a third reading indicative of a third thermal transport property of the mixture during the second transient time period or when the heating element is at the third temperature; and
determining, based additionally on the third reading, the concentration of the component of the mixture.

16. The method according to claim 15, wherein at least one of the first transient time period and the second transient time period is a cooling transient time period.

17. A method according to claim 11, further comprising:

changing a temperature of a second heating element from the first temperature to the second temperature over the first transient time period, the second heating element being thermally insulated from the first heating element and located in a reference atmosphere;

obtaining a first reference reading indicative of a first thermal transport property of the reference environment during the first transient time period;

obtaining a second reference reading indicative of a second thermal transport property of the reference environment when the second heating element is at the second temperature; and determining the concentration of the component of the mixture based additionally on the first reference reading and the second reference reading.

18. The method according to claim 11, further comprising:

changing a temperature of a second heating element from a fourth temperature to a fifth temperature over a further first transient time period, the fifth temperature being different from the second temperature, the second heating element being thermally insulated from the first heating element; and obtaining a fourth reading indicative of a fourth thermal transport property of the mixture during the further first transient time period or when the second heating element is at the fifth temperature.

19. The method according to claim 18 wherein the first transient time period and the further first transient time period have a same length.

20. The method according to claim 18, wherein the fifth temperature is equal to the first temperature.

* * * * *